US008541389B2

(12) United States Patent
Yanni et al.

(10) Patent No.: US 8,541,389 B2
(45) Date of Patent: *Sep. 24, 2013

(54) RNAI-MEDIATED INHIBITION OF TUMOR NECROSIS FACTOR α-RELATED CONDITIONS

(75) Inventors: John M. Yanni, Burleson, TX (US); Jon E. Chatterton, Fort Worth, TX (US); Diane Michelle Senchyna, Fort Worth, TX (US); Daniel A. Gamache, Arlington, TX (US); Steven T. Miller, Arlington, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 139 days.

This patent is subject to a terminal disclaimer.

(21) Appl. No.: 13/035,147

(22) Filed: Feb. 25, 2011

(65) Prior Publication Data

US 2011/0142767 A1  Jun. 16, 2011

Related U.S. Application Data

(62) Division of application No. 12/700,188, filed on Feb. 4, 2010, now abandoned, which is a division of application No. 11/750,262, filed on May 17, 2007, now Pat. No. 7,732,421.

(60) Provisional application No. 60/801,788, filed on May 19, 2006.

(51) Int. Cl.
*C12N 15/11* (2006.01)

(52) U.S. Cl.
USPC ....................................................... 514/44 A

(58) Field of Classification Search
USPC ....................................................... 514/44 A
See application file for complete search history.

(56) References Cited

U.S. PATENT DOCUMENTS

| 6,506,559 B1 | 1/2003 | Fire et al. |
| 6,573,099 B2 | 6/2003 | Graham |
| 2005/0227935 A1 | 10/2005 | McSwiggen et al. |
| 2005/0246794 A1 | 11/2005 | Khvorova |
| 2006/0189564 A1 | 8/2006 | Burright et al. |
| 2007/0281901 A1 | 12/2007 | Yanni et al. |
| 2008/0113351 A1* | 5/2008 | Naito et al. ............ 435/6 |

FOREIGN PATENT DOCUMENTS

| WO | 0027421 | 5/2000 |
| WO | 0130360 A1 | 3/2001 |
| WO | 0130395 A1 | 3/2001 |
| WO | 0248168 A1 | 6/2002 |
| WO | 2004056858 A2 | 7/2004 |
| WO | 2004080406 A2 | 9/2004 |
| WO | 2004113387 A2 | 12/2004 |
| WO | 2007137129 A2 | 11/2007 |

OTHER PUBLICATIONS

Nguyen et al (Curr. Opin. Mol. Ther. 10(2): 158-167, 2008).*
Cejka et al (Clinical Science 110: 47-58, 2006).*
Hangai et al. (Journal of Neuroimmunology 171:45-56, Feb. 2006).*
Limb et al. (Clin. Exp. Immunol. 115:409-414,1999).*
Campochiaro et al. (Gene Therapy 13, 559-562, Mar. 2006).*
Reich et al.(Molecular Vision 9,210-216, 2003).*
Bandyopadhyay, et al; "Interleukin-1alpha stimulates non-amyloidogenic pathway by alpha-secretase (ADAM-10 and ADAM-17) cleavage of APP in human astrocytic cells involving p38 MAP kinase"; Jul. 2006; vol. 84; No. 1; pp. 106-118.
Castanotto, et al., "Functional siRNA expression from transfected PCR products"; 2002; vol. 8; pp. 1454-1460; RNA.
Chen, et al.; "Urothelial lesion formation is mediated by TNRF1 during neurogenic cystitis"; Oct. 2006; vol. 291; No. 4; pp. F741-F749; American Journal of Physiology, Renal Physiology.
Franchimont, et al. "Interleukin-6 receptor shedding is enhanced by interleukin-1beta and tumor necrosis factor alpha and is partially mediated by tumor necrosis factor alpha-converting enzyme in osteoblast-like cells"; Jan. 2005; vol. 52; No. 1; pp. 84-93; Arthritis and Rheumatism.
Hu, et al.; "Autocrine tumor necrosis factor alpha links endoplasmic reticulum stress to the membrane death receptor pathway through IRE1alpha-mediated NF-kappaB activation, and down-regulation of TRAF2 expression"; Apr. 2006; vol. 26; No. 8; pp. 3071-3084; Molecular and Cellular Biology.
Kim, et al.; "Synthetic dsRNA dicer substrates enhance RNAi potency and efficacy" Feb. 2005; vol. 23; No. 2; pp. 222-226; Nature Biotechnology.
Kenny, et al.; Targeting TACE-dependent EGFR ligand shedding in breast cancer; Feb. 2007; vol. 117; No. 2; pp. 337-345; The Journal of Clinical Investigation.
Marsh, et al.; "Topical nonpreserved methylprednisolone therapy for keratoconjunctivitis sicca in sjogren syndrome" Apr. 1999; vol. 106; No. 4; pp. 811-816; Ophthalmology.
Offord, et al.; "Immortalized human corneal epithelial cells for ocular toxicity and inflammation studies" May 1999; vol. 40; No. 6; pp. 1091-1101; Investigative Ophthalmology & Vision Science.
Shao, et al.; "Cigarette smoke induces MUC5A Mucin overproduction via tumor necrosis factor-alpha-converting enzyme in human airway epithelial (NCI-H292) cells"; Aug. 2004; vol. 287; No. 2; pp. L420-L427; American Journal of Physiology, Lung Cellular and Molecular Physiology.
Singh, et al., "Cytokine stimulated vascular cell adhesion molecule-1 (VCAM-1) ectodomain release is regulated by TIMP-3", Jul. 1, 2005; vol. 67; No. 1; pp. 39-49; Cardiovascular Research.

(Continued)

*Primary Examiner* — Brian Whiteman
(74) *Attorney, Agent, or Firm* — Jason J. Derry

(57) ABSTRACT

RNA interference is provided for inhibition of tumor necrosis factor α (TNFα) by silencing TNFα cell surface receptor TNF receptor-1 (TNFR1) mRNA expression, or by silencing TNFα converting enzyme (TACE/ADAM17) mRNA expression. Silencing such TNFα targets, in particular, is useful for treating patients having a TNFα-related condition or at risk of developing a TNFα-related condition such as the ocular conditions dry eye, allergic conjunctivitis, or ocular inflammation, or such as dermatitis, rhinitis, or asthma, for example.

6 Claims, 1 Drawing Sheet

(56) References Cited

OTHER PUBLICATIONS

Sutheesopon, et al.; Involvement of the tumor necrosis factor (TNF)/TNF receptor system in leukemic cell apoptosis induced by histone deacetylase inhibitor depsipeptide; May 2005; vol. 203; No. 2; pp. 387-397; Journal of Cellular Physiology.

Zhan, et al.; "TACE release of TNF-alpha mediates mechanotransduction-induced activation of p38 MAPK and myogenesis"; Feb. 2007; vol. 120; No. Pt 4; pp. 692-701; Journal of Cell Science.

Nakamura, et al.; "RNA interference targeting transforming growth factor-beta type II receptor suppresses ocular inflammation and fibrosis"; Molecular Vision; vol. 10; pp. 703-711 (2004).

Steely, et al.; "Protein expression in a transformed trabecular meshwork cell line: proteome analysis"; Molecular Vision; vol. 12; pp. 372-383 (2006).

Lindstedt et al.; "Anti-TNF-alpha therapy for sight threatening uveitis"; Scientific Report; Br. J. Ophthalmol; vol. 89; pp. 533-536 (2005).

International Search Report, Written Opinion and IPER for corresponding PCT application No. PCT/US2007/069165.

* cited by examiner

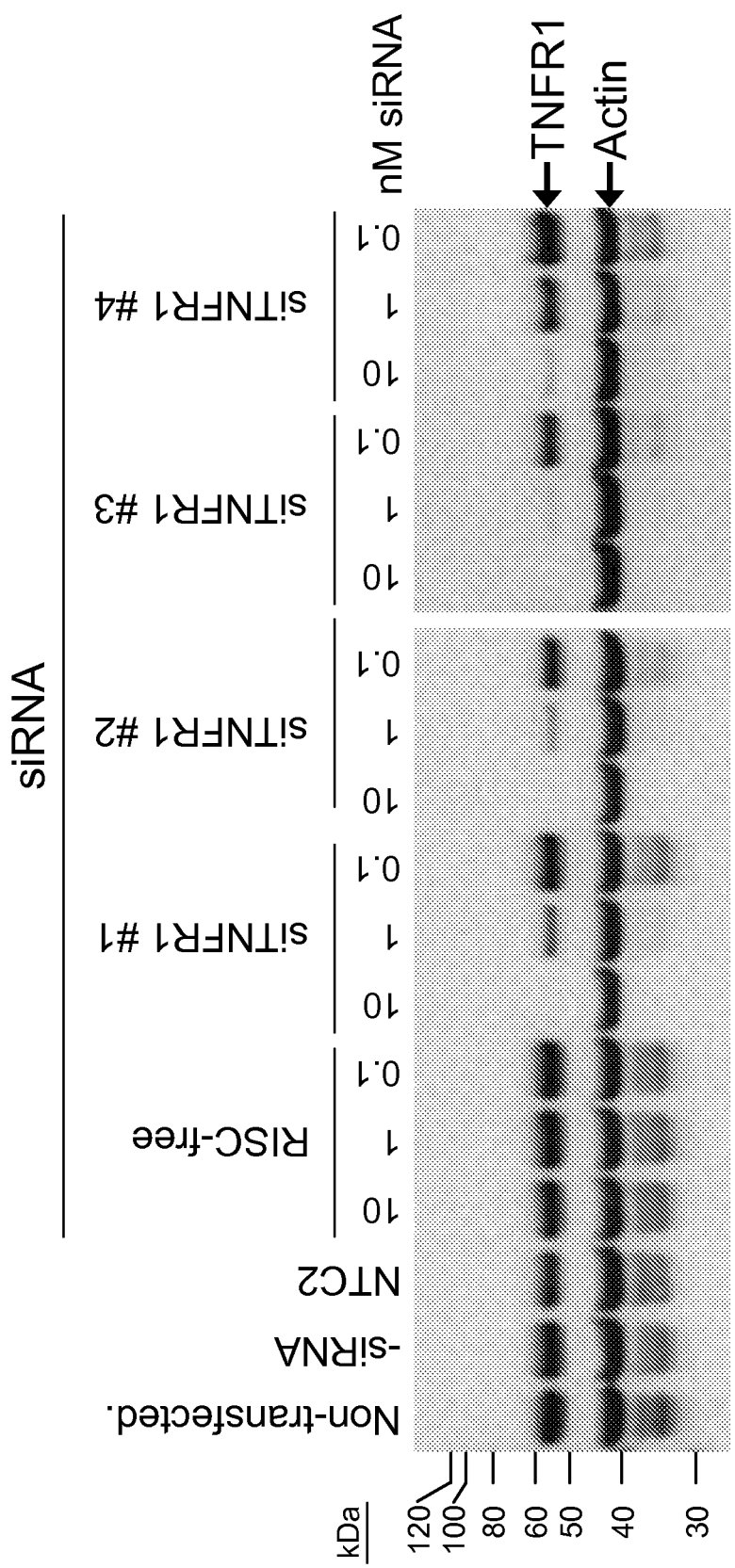

SEQUENCE LISTING

<160> NUMBER OF SEQ ID NOS: 205

<210> SEQ ID NO 1
<211> LENGTH: 3572
<212> TYPE: DNA
<213> ORGANISM: Homo sapiens

<400> SEQUENCE: 1

| | | | | | |
|---|---|---|---|---|---|
| acctgcactt | ctgggggcgt | cgagcctggc | ggtagaatct | tcccagtagg cggcgcggga | 60 |
| gggaaaagag | gattgagggg | ctaggccggg | cggatcccgt | cctcccccga tgtgagcagt | 120 |
| tttccgaaac | cccgtcaggc | gaaggctgcc | cagagaggtg | gagtcggtag cggggccggg | 180 |
| aacatgaggc | agtctctcct | attcctgacc | agcgtggttc | ctttcgtgct ggcgccgcga | 240 |
| cctccggatg | acccgggctt | cggcccccac | cagagactcg | agaagcttga ttctttgctc | 300 |
| tcagactacg | atattctctc | tttatctaat | atccagcagc | attcggtaag aaaaagagat | 360 |
| ctacagactt | caacacatgt | agaaacacta | ctaactttt | cagctttgaa aaggcatttt | 420 |
| aaattatacc | tgcatcaag | tactgaacgt | ttttcacaaa | atttcaaggt cgtggtggtg | 480 |
| gatggtaaaa | acgaaagcga | gtacactgta | aaatggcagg | acttcttcac tggacacgtg | 540 |
| gttggtgagc | ctgactctag | ggttctagcc | cacataagag | atgatgatgt tataatcaga | 600 |
| atcaacacag | atggggccga | atataacata | gagccacttt | ggagatttgt taatgatacc | 660 |
| aaagacaaaa | gaatgttagt | ttataaatct | gaagatatca | agaatgtttc acgtttgcag | 720 |
| tctccaaaag | tgtgtggtta | tttaaaagtg | gataatgaag | agttgctccc aaaagggtta | 780 |
| gtagacagaa | aaccacctga | agagcttgtt | catcgagtga | aaagaagagc tgacccagat | 840 |
| cccatgaaga | acacgtgtaa | attattggtg | gtagcagatc | atcgcttcta cagatacatg | 900 |
| ggcagagggg | aagagagtac | aactacaaat | tacttaatag | agctaattga cagagttgat | 960 |
| gacatctatc | ggaacacttc | atgggataat | gcaggtttta | aaggctatgg aatacagata | 1020 |
| gagcagattc | gcattctcaa | gtctccacaa | gaggtaaaac | ctggtgaaaa gcactacaac | 1080 |
| atggcaaaaa | gttacccaaa | tgaagaaaag | gatgcttggg | atgtgaagat gttgctagag | 1140 |
| caatttagct | ttgatatagc | tgaggaagca | tctaaagttt | gcttggcaca ccttttcaca | 1200 |
| taccaagatt | ttgatatggg | aactcttgga | ttagcttatg | ttggctctcc cagagcaaac | 1260 |
| agccatggag | gtgtttgtcc | aaaggcttat | tatagcccag | ttgggaagaa aaatatctat | 1320 |
| ttgaatagtg | gtttgacgag | cacaaagaat | tatggtaaaa | ccatccttac aaaggaagct | 1380 |
| gacctggtta | caactcatga | attgggacat | aattttggag | cagaacatga tccggatggt | 1440 |
| ctagcagaat | gtgccccgaa | tgaggaccag | ggagggaaat | atgtcatgta tcccatagct | 1500 |
| gtgagtggcg | atcacgagaa | caataagatg | ttttcaaact | gcagtaaaca atcaatctat | 1560 |
| aagaccattg | aaagtaaggc | ccaggagtgt | tttcaagaac | gcagcaataa agtttgtggg | 1620 |
| aactcgaggg | tggatgaagg | agaagagtgt | gatcctggca | tcatgtatct gaacaacgac | 1680 |
| acctgctgca | cagcgactg | cacgttgaag | gaaggtgtcc | agtgcagtga caggaacagt | 1740 |
| ccttgctgta | aaaactgtca | gtttgagact | gcccagaaga | agtgccagga ggcgattaat | 1800 |
| gctacttgca | aaggcgtgtc | ctactgcaca | ggtaatagca | gtgagtgccc gcctccagga | 1860 |
| aatgctgaag | atgacactgt | ttgcttggat | cttggcaagt | gtaaggatgg aaatgcatc | 1920 |
| cctttctgcg | agagggaaca | gcagctggag | tcctgtgcat | gtaatgaaac tgacaactcc | 1980 |
| tgcaaggtgt | gctgcaggga | cctttctggc | cgctgtgtgc | cctatgtcga tgctgaacaa | 2040 |

```
aagaacttat ttttgaggaa aggaaagccc tgtacagtag gattttgtga catgaatggc    2100
aaatgtgaga aacgagtaca ggatgtaatt gaacgatttt gggatttcat tgaccagctg    2160
agcatcaata cttttggaaa gttttagca gacaacatcg ttgggtctgt cctggtttc    2220 tccttgatat tttggattcc tttcagcatt cttgtccatt gtgtggataa gaaattggat    2280
aaacagtatg aatctctgtc tctgtttcac cccagtaacg tcgaaatgct gagcagcatg    2340
gattctgcat cggttcgcat tatcaaaccc tttcctgcgc cccagactcc aggccgcctg    2400
cagcctgccc ctgtgatccc ttcggcgcca gcagctccaa aactggacca ccagagaatg    2460
gacaccatcc aggaagaccc cagcacagac tcacatatgg acgaggatgg gtttgagaag    2520
gaccccttcc caaatagcag cacagctgcc aagtcatttg aggatctcac ggaccatccg    2580
gtcaccagaa gtgaaaaggc tgcctccttt aaactgcagc gtcagaatcg tgttgacagc    2640
aaagaaacag agtgctaatt tagttctcag ctcttctgac ttaagtgtgc aaaatatttt    2700
tatagatttg acctacaaat caatcacagc ttgtattttg tgaagactgg gaagtgactt    2760
agcagatgct ggtcatgtgt ttgaacttcc tgcaggtaaa cagttcttgt gtggtttggc    2820
ccttctcctt ttgaaaaggt aaggtgaagg tgaatctagc ttattttgag gctttcaggt    2880
tttagttttt aaaatatctt ttgacctgtg gtgcaaaagc agaaaataca gctggattgg    2940
gttatgaata tttacgtttt tgtaaattaa tcttttatat tgataacagc actgactagg    3000
gaaatgatca gttttttttt atacactgta atgaaccgct gaatatgagg catttggcat    3060
ttatttgtga tgcaactgg aatagttttt ttttttttt tttttttg ccttcaacta    3120 aaaacaaagg agataaatct agtatacatt gtctctaaat tgtgggtcta tttctagtta    3180
ttacccagag tttttatgta gcagggaaaa tatatatcta aatttagaaa tcatttgggt    3240
taatatggct cttcataatt ctaagactaa tgctctctag aaacctaacc acctaccta    3300 cagtgagggc tatacatggt agccagttga atttatggaa tctaccaact gtttagggcc    3360
ctgatttgct gggcagtttt tctgtatttt ataagtatct tcatgtatcc ctgttactga    3420
tagggataca tgctcttaga aaattcacta ttggctggga gtggtggctc atgcctgtaa    3480
tcccagcact tggagaggct gaggttgcgc cactacactc cagcctgggt gacagagtga    3540
gactctgcct caaaaaaaaa aaaaaaaaa aa    3572
```

<210> SEQ ID NO 2  
<211> LENGTH: 2236  
<212> TYPE: DNA  
<213> ORGANISM: Homo sapiens
<400> SEQUENCE: 2

```
gctgttgcaa cactgcctca ctcttcccct cccaccttct ctccctcct ctctgcttta      60 attttctcag aattctctgg actgaggctc cagttctggc ctttggggtt caagatcact     120
gggaccaggc cgtgatctct atgcccgagt ctcaaccctc aactgtcacc caaggcact     180 tgggacgtcc tggacagacc gagtcccggg aagccccagc actgccgctg ccacactgcc     240
ctgagcccaa atgggggagt gagaggccat agctgtctgg catgggcctc tccaccgtgc     300
ctgacctgct gctgccactg gtgctcctgg agctgttggt gggaatatac ccctcagggg     360
ttattggact ggtccctcac ctaggggaca gggagaagag agatagtgtg tgtccccaag     420
gaaaatatat ccaccctcaa ataattcga tttgctgtac caagtgccac aaaggaacct     480
acttgtacaa tgactgtcca ggcccggggc aggatacgga ctgcagggag tgtgagagcg     540
gctccttcac cgcttcagaa aaccacctca gacactgcct cagctgctcc aaatgccgaa     600
```

-continued

```
aggaaatggg tcaggtggag atctcttctt gcacagtgga ccgggacacc gtgtgtggct      660
gcaggaagaa ccagtaccgg cattattgga gtgaaaacct tttccagtgc ttcaattgca      720
gcctctgcct caatgggacc gtgcacctct cctgccagga gaaacagaac accgtgtgca      780
cctgccatgc aggtttcttt ctaagagaaa acgagtgtgt ctcctgtagt aactgtaaga      840
aaagcctgga gtgcacgaag ttgtgcctac cccagattga gaatgttaag ggcactgagg      900
actcaggcac cacagtgctg ttgccctgg tcatttttct tggtctttgc cttttatccc       960
tcctcttcat tggtttaatg tatcgctacc aacggtggaa gtccaagctc tactccattg     1020
tttgtgggaa atcgacacct gaaaagagg gggagcttga aggaactact actaagcccc      1080
tggccccaaa cccaagcttc agtcccactc caggcttcac ccccacccctg ggcttcagtc    1140 ccgtgcccag ttccaccttc acctccagct ccacctatac ccccggtgac tgtcccaact    1200
ttgcggctcc ccgcagagag gtggcaccac cctatcaggg ggctgacccc atccttgcga    1260
cagccctcgc ctccgacccc atccccaacc cccttcagaa gtgggaggac agcgcccaca    1320
agccacagag cctagacact gatgaccccg cgacgctgta cgccgtggtg gagaacgtgc    1380
ccccgttgcg ctggaaggaa ttcgtgcggg gcctagggct gagcgaccac gagatcgatc    1440
ggctggagct gcagaacggg cgctgcctgc gcgaggcgca atacagcatg ctggcgacct    1500
ggaggcggcg cacgccgcgg cgcgaggcca cgctggagct gctgggacgc gtgctccgcg    1560
acatggacct gctgggctgc ctggaggaca tcgaggaggc gctttgcggc cccgccgccc    1620
tcccgcccgc gcccagtctt tcagatgag gctgcgcccc tgcgggcagc tctaaggacc     1680
gtcctgcgag atcgccttcc aaccccactt ttttctggaa aggaggggtc ctgcaggggc    1740
aagcaggagc tagcagccgc ctacttggtg ctaacccctc gatgtacata gcttttctca    1800
gctgcctgcg cgccgccgac agtcagcgct gtgcgcgcgg agagaggtgc gccgtgggct    1860
caagagcctg agtgggtggt ttgcgaggat gagggacgct atgcctcatg cccgttttgg    1920
gtgtcctcac cagcaaggct gctcggggc ccctggttcg tccctgagcc ttttttcacag    1980 tgcataagca gttttttttg tttttgtttt gttttgtttt gtttttaaat caatcatgtt     2040
acactaatag aaacttggca ctcctgtgcc ctctgcctgg acaagcacat agcaagctga    2100
actgtcctaa ggcaggggcg agcacggaac aatgggggcct tcagctggag ctgtggactt    2160
ttgtacatac actaaaattc tgaagttaaa gctctgctct tggaaaaaaa aaaaaaaaaa    2220
aaaaaaaaaa aaaaaa                                                      2236
```

<210> SEQ ID NO 3
<211> LENGTH: 19
<212> TYPE: DNA
<213> ORGANISM: Artificial
<220> FEATURE:
<223> OTHER INFORMATION: Target Sequence

<400> SEQUENCE: 3

```
gctctcagac tacgatatt                                                     19
```

<210> SEQ ID NO 4
<211> LENGTH: 21
<212> TYPE: DNA
<213> ORGANISM: Artificial
<220> FEATURE:
<223> OTHER INFORMATION: Sense Strand with 3'NN
<220> FEATURE:
<221> NAME/KEY: misc_RNA
<222> LOCATION: (1)..(19)
<223> OTHER INFORMATION: ribonucleotides
<220> FEATURE:

```
<221> NAME/KEY: misc_feature
<222> LOCATION: (20)..(21)
<223> OTHER INFORMATION: any, A, T/U, C, G

<400> SEQUENCE: 4
gcucucagac uacgauauun n                                              21

<210> SEQ ID NO 5
<211> LENGTH: 21
<212> TYPE: DNA
<213> ORGANISM: Artificial
<220> FEATURE:
<223> OTHER INFORMATION: Antisense strand with 3'NN
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: any, A, T/U, C, G

<400> SEQUENCE: 5
aauaucguag ucugagagcn n                                              21

<210> SEQ ID NO 6
<211> LENGTH: 21
<212> TYPE: RNA
<213> ORGANISM: Artificial
<220> FEATURE:
<223> OTHER INFORMATION: Sense Strand

<400> SEQUENCE: 6
gcucucagac uacgauauuu u                                              21

<210> SEQ ID NO 7
<211> LENGTH: 21
<212> TYPE: RNA
<213> ORGANISM: Artificial
<220> FEATURE:
<223> OTHER INFORMATION: Antisense Strand

<400> SEQUENCE: 7
aauaucguag ucugagagcu u                                              21

<210> SEQ ID NO 8
<211> LENGTH: 19
<212> TYPE: RNA
<213> ORGANISM: Artificial
<220> FEATURE:
<223> OTHER INFORMATION: Sense Strand

<400> SEQUENCE: 8
gcucucagac uacgauauu                                                 19

<210> SEQ ID NO 9
<211> LENGTH: 19
<212> TYPE: RNA
<213> ORGANISM: Artificial
<220> FEATURE:
<223> OTHER INFORMATION: Antisense Strand

<400> SEQUENCE: 9
aauaucguag ucugagagc                                                 19

<210> SEQ ID NO 10
<211> LENGTH: 48
<212> TYPE: DNA
```

```
<213> ORGANISM: Artificial
<220> FEATURE:
<223> OTHER INFORMATION: Hairpin duplex with loop
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(27)
<223> OTHER INFORMATION: any, A, T/U, C, G
<220> FEATURE:
<221> NAME/KEY: misc_feature
<222> LOCATION: (28)..(48)
<223> OTHER INFORMATION: ribonucleotides

<400> SEQUENCE: 10
gcucucagac uacgauauun nnnnnnnaau aucguagucu gagagcuu         48

<210> SEQ ID NO 11
<211> LENGTH: 25
<212> TYPE: DNA
<213> ORGANISM: Artificial
<220> FEATURE:
<223> OTHER INFORMATION: Sense Strand

<400> SEQUENCE: 11
gcucucagac uacgauauuc ucucu                                  25

<210> SEQ ID NO 12
<211> LENGTH: 25
<212> TYPE: RNA
<213> ORGANISM: Artificial
<220> FEATURE:
<223> OTHER INFORMATION: Sense Strand

<400> SEQUENCE: 12
gcucucagac uacgauauuc ucucu                                  25

<210> SEQ ID NO 13
<211> LENGTH: 27
<212> TYPE: RNA
<213> ORGANISM: Artificial
<220> FEATURE:
<223> OTHER INFORMATION: Antisense Strand

<400> SEQUENCE: 13
agagagaaua ucguagucug agagcuu                                27

<210> SEQ ID NO 14
<211> LENGTH: 19
<212> TYPE: DNA
<213> ORGANISM: Artificial
<220> FEATURE:
<223> OTHER INFORMATION: Target Sequence

<400> SEQUENCE: 14
ccagcagcat tcggtaaga                                         19

<210> SEQ ID NO 15
<211> LENGTH: 19
<212> TYPE: DNA
<213> ORGANISM: Artificial
<220> FEATURE:
<223> OTHER INFORMATION: Target Sequence

<400> SEQUENCE: 15
cagcagcatt cggtaagaa                                         19
```

```
<210> SEQ ID NO 16
<211> LENGTH: 19
<212> TYPE: DNA
<213> ORGANISM: Artificial
<220> FEATURE:
<223> OTHER INFORMATION: Target Sequence

<400> SEQUENCE: 16
agcagcattc ggtaagaaa                                                  19

<210> SEQ ID NO 17
<211> LENGTH: 19
<212> TYPE: DNA
<213> ORGANISM: Artificial
<220> FEATURE:
<223> OTHER INFORMATION: Target Sequence

<400> SEQUENCE: 17
agagatctac agacttcaa                                                  19

<210> SEQ ID NO 18
<211> LENGTH: 19
<212> TYPE: DNA
<213> ORGANISM: Artificial
<220> FEATURE:
<223> OTHER INFORMATION: Target Sequence

<400> SEQUENCE: 18
gaaagcgagt acactgtaa                                                  19

<210> SEQ ID NO 19
<211> LENGTH: 19
<212> TYPE: DNA
<213> ORGANISM: Artificial
<220> FEATURE:
<223> OTHER INFORMATION: Target Sequence

<400> SEQUENCE: 19
ccatgaagaa cacgtgtaa                                                  19

<210> SEQ ID NO 20
<211> LENGTH: 19
<212> TYPE: DNA
<213> ORGANISM: Artificial
<220> FEATURE:
<223> OTHER INFORMATION: Target Sequence

<400> SEQUENCE: 20
gaagaacacg tgtaaatta                                                  19

<210> SEQ ID NO 21
<211> LENGTH: 19
<212> TYPE: DNA
<213> ORGANISM: Artificial
<220> FEATURE:
<223> OTHER INFORMATION: Target Sequence

<400> SEQUENCE: 21
atcatcgctt ctacagata                                                  19

<210> SEQ ID NO 22
<211> LENGTH: 19
<212> TYPE: DNA
<213> ORGANISM: Artificial
<220> FEATURE:
<223> OTHER INFORMATION: Target Sequence
```

<400> SEQUENCE: 22
agagcaattt agctttgat                                              19

<210> SEQ ID NO 23
<211> LENGTH: 19
<212> TYPE: DNA
<213> ORGANISM: Artificial
<220> FEATURE:
<223> OTHER INFORMATION: Target Sequence

<400> SEQUENCE: 23
ggtttgacga gcacaaaga                                              19

<210> SEQ ID NO 24
<211> LENGTH: 19
<212> TYPE: DNA
<213> ORGANISM: Artificial
<220> FEATURE:
<223> OTHER INFORMATION: Target Sequence

<400> SEQUENCE: 24
tgatccggat ggtctagca                                              19

<210> SEQ ID NO 25
<211> LENGTH: 19
<212> TYPE: DNA
<213> ORGANISM: Artificial
<220> FEATURE:
<223> OTHER INFORMATION: Target Sequence

<400> SEQUENCE: 25
gcgatcacga gaacaataa                                              19

<210> SEQ ID NO 26
<211> LENGTH: 19
<212> TYPE: DNA
<213> ORGANISM: Artificial
<220> FEATURE:
<223> OTHER INFORMATION: Target Sequence

<400> SEQUENCE: 26
gcagtaaaca atcaatcta                                              19

<210> SEQ ID NO 27
<211> LENGTH: 19
<212> TYPE: DNA
<213> ORGANISM: Artificial
<220> FEATURE:
<223> OTHER INFORMATION: Target Sequence

<400> SEQUENCE: 27
caatctataa gaccattga                                              19

<210> SEQ ID NO 28
<211> LENGTH: 19
<212> TYPE: DNA
<213> ORGANISM: Artificial
<220> FEATURE:
<223> OTHER INFORMATION: Target Sequence

<400> SEQUENCE: 28
tttcaagaac gcagcaata                                              19

<210> SEQ ID NO 29
<211> LENGTH: 19
<212> TYPE: DNA

-continued

```
<213> ORGANISM: Artificial
<220> FEATURE:
<223> OTHER INFORMATION: Target Sequence

<400> SEQUENCE: 29
ttcaagaacg cagcaataa                                                19

<210> SEQ ID NO 30
<211> LENGTH: 19
<212> TYPE: DNA
<213> ORGANISM: Artificial
<220> FEATURE:
<223> OTHER INFORMATION: Target Sequence

<400> SEQUENCE: 30
tcaagaacgc agcaataaa                                                19

<210> SEQ ID NO 31
<211> LENGTH: 19
<212> TYPE: DNA
<213> ORGANISM: Artificial
<220> FEATURE:
<223> OTHER INFORMATION: Target Sequence

<400> SEQUENCE: 31
tcatgtatct gaacaacga                                                19

<210> SEQ ID NO 32
<211> LENGTH: 19
<212> TYPE: DNA
<213> ORGANISM: Artificial
<220> FEATURE:
<223> OTHER INFORMATION: Target Sequence

<400> SEQUENCE: 32
acagcgactg cacgttgaa                                                19

<210> SEQ ID NO 33
<211> LENGTH: 19
<212> TYPE: DNA
<213> ORGANISM: Artificial
<220> FEATURE:
<223> OTHER INFORMATION: Target Sequence

<400> SEQUENCE: 33
gattaatgct acttgcaaa                                                19

<210> SEQ ID NO 34
<211> LENGTH: 19
<212> TYPE: DNA
<213> ORGANISM: Artificial
<220> FEATURE:
<223> OTHER INFORMATION: Target Sequence

<400> SEQUENCE: 34
ctggagtcct gtgcatgta                                                19

<210> SEQ ID NO 35
<211> LENGTH: 19
<212> TYPE: DNA
<213> ORGANISM: Artificial
<220> FEATURE:
<223> OTHER INFORMATION: Target Sequence

<400> SEQUENCE: 35
tggagtcctg tgcatgtaa                                                19
```

```
<210> SEQ ID NO 36
<211> LENGTH: 19
<212> TYPE: DNA
<213> ORGANISM: Artificial
<220> FEATURE:
<223> OTHER INFORMATION: Target Sequence

<400> SEQUENCE: 36
ggagtcctgt gcatgtaat                                             19

<210> SEQ ID NO 37
<211> LENGTH: 19
<212> TYPE: DNA
<213> ORGANISM: Artificial
<220> FEATURE:
<223> OTHER INFORMATION: Target Sequence

<400> SEQUENCE: 37
catgtaatga aactgacaa                                             19

<210> SEQ ID NO 38
<211> LENGTH: 19
<212> TYPE: DNA
<213> ORGANISM: Artificial
<220> FEATURE:
<223> OTHER INFORMATION: Target Sequence

<400> SEQUENCE: 38
ctatgtcgat gctgaacaa                                             19

<210> SEQ ID NO 39
<211> LENGTH: 19
<212> TYPE: DNA
<213> ORGANISM: Artificial
<220> FEATURE:
<223> OTHER INFORMATION: Target Sequence

<400> SEQUENCE: 39
caaatgtgag aaacgagta                                             19

<210> SEQ ID NO 40
<211> LENGTH: 19
<212> TYPE: DNA
<213> ORGANISM: Artificial
<220> FEATURE:
<223> OTHER INFORMATION: Target Sequence

<400> SEQUENCE: 40
gcatcggttc gcattatca                                             19

<210> SEQ ID NO 41
<211> LENGTH: 19
<212> TYPE: DNA
<213> ORGANISM: Artificial
<220> FEATURE:
<223> OTHER INFORMATION: Target Sequence

<400> SEQUENCE: 41
atcggttcgc attatcaaa                                             19

<210> SEQ ID NO 42
<211> LENGTH: 19
<212> TYPE: DNA
<213> ORGANISM: Artificial
<220> FEATURE:
<223> OTHER INFORMATION: Target Sequence
```

-continued

```
<400> SEQUENCE: 42
ccaagtcatt tgaggatct                                                     19

<210> SEQ ID NO 43
<211> LENGTH: 19
<212> TYPE: DNA
<213> ORGANISM: Artificial
<220> FEATURE:
<223> OTHER INFORMATION: Target Sequence

<400> SEQUENCE: 43
ccggtcacca gaagtgaaa                                                     19

<210> SEQ ID NO 44
<211> LENGTH: 19
<212> TYPE: DNA
<213> ORGANISM: Artificial
<220> FEATURE:
<223> OTHER INFORMATION: Target Sequence

<400> SEQUENCE: 44
aaaggctgcc tcctttaaa                                                     19

<210> SEQ ID NO 45
<211> LENGTH: 19
<212> TYPE: DNA
<213> ORGANISM: Artificial
<220> FEATURE:
<223> OTHER INFORMATION: Target Sequence

<400> SEQUENCE: 45
tttaaactgc agcgtcaga                                                     19

<210> SEQ ID NO 46
<211> LENGTH: 19
<212> TYPE: DNA
<213> ORGANISM: Artificial
<220> FEATURE:
<223> OTHER INFORMATION: Target Sequence

<400> SEQUENCE: 46
agatgctggt catgtgttt                                                     19

<210> SEQ ID NO 47
<211> LENGTH: 19
<212> TYPE: DNA
<213> ORGANISM: Artificial
<220> FEATURE:
<223> OTHER INFORMATION: Target Sequence

<400> SEQUENCE: 47
atgctggtca tgtgtttga                                                     19

<210> SEQ ID NO 48
<211> LENGTH: 19
<212> TYPE: DNA
<213> ORGANISM: Artificial
<220> FEATURE:
<223> OTHER INFORMATION: Target Sequence

<400> SEQUENCE: 48
tgctggtcat gtgtttgaa                                                     19

<210> SEQ ID NO 49
<211> LENGTH: 19
<212> TYPE: DNA
```

-continued

```
<213> ORGANISM: Artificial
<220> FEATURE:
<223> OTHER INFORMATION: Target Sequence

<400> SEQUENCE: 49
ctggtcatgt gtttgaact                                                       19

<210> SEQ ID NO 50
<211> LENGTH: 19
<212> TYPE: DNA
<213> ORGANISM: Artificial
<220> FEATURE:
<223> OTHER INFORMATION: Target Sequence

<400> SEQUENCE: 50
tgtaatgaac cgctgaata                                                       19

<210> SEQ ID NO 51
<211> LENGTH: 19
<212> TYPE: DNA
<213> ORGANISM: Artificial
<220> FEATURE:
<223> OTHER INFORMATION: Target Sequence

<400> SEQUENCE: 51
gtaatgaacc gctgaatat                                                       19

<210> SEQ ID NO 52
<211> LENGTH: 19
<212> TYPE: DNA
<213> ORGANISM: Artificial
<220> FEATURE:
<223> OTHER INFORMATION: Target Sequence

<400> SEQUENCE: 52
ctaagactaa tgctctcta                                                       19

<210> SEQ ID NO 53
<211> LENGTH: 19
<212> TYPE: DNA
<213> ORGANISM: Artificial
<220> FEATURE:
<223> OTHER INFORMATION: Target Sequence

<400> SEQUENCE: 53
agactaatgc tctctagaa                                                       19

<210> SEQ ID NO 54
<211> LENGTH: 19
<212> TYPE: DNA
<213> ORGANISM: Artificial
<220> FEATURE:
<223> OTHER INFORMATION: Target Sequence

<400> SEQUENCE: 54
cctaaccacc taccttaca                                                       19

<210> SEQ ID NO 55
<211> LENGTH: 19
<212> TYPE: DNA
<213> ORGANISM: Artificial
<220> FEATURE:
<223> OTHER INFORMATION: Target Sequence

<400> SEQUENCE: 55
tacatggtag ccagttgaa                                                       19
```

```
<210> SEQ ID NO 56
<211> LENGTH: 19
<212> TYPE: DNA
<213> ORGANISM: Artificial
<220> FEATURE:
<223> OTHER INFORMATION: Target Sequence

<400> SEQUENCE: 56
tggtagccag ttgaattta                                               19

<210> SEQ ID NO 57
<211> LENGTH: 19
<212> TYPE: DNA
<213> ORGANISM: Artificial
<220> FEATURE:
<223> OTHER INFORMATION: Target Sequence

<400> SEQUENCE: 57
tttatggaat ctaccaact                                               19

<210> SEQ ID NO 58
<211> LENGTH: 19
<212> TYPE: DNA
<213> ORGANISM: Artificial
<220> FEATURE:
<223> OTHER INFORMATION: Target Sequence

<400> SEQUENCE: 58
ggaatctacc aactgttta                                               19

<210> SEQ ID NO 59
<211> LENGTH: 19
<212> TYPE: DNA
<213> ORGANISM: Artificial
<220> FEATURE:
<223> OTHER INFORMATION: Target Sequence

<400> SEQUENCE: 59
accaggccgt gatctctat                                               19

<210> SEQ ID NO 60
<211> LENGTH: 19
<212> TYPE: DNA
<213> ORGANISM: Artificial
<220> FEATURE:
<223> OTHER INFORMATION: Target Sequence

<400> SEQUENCE: 60
aattcgattt gctgtacca                                               19

<210> SEQ ID NO 61
<211> LENGTH: 19
<212> TYPE: DNA
<213> ORGANISM: Artificial
<220> FEATURE:
<223> OTHER INFORMATION: Target Sequence

<400> SEQUENCE: 61
tcgatttgct gtaccaagt                                               19

<210> SEQ ID NO 62
<211> LENGTH: 19
<212> TYPE: DNA
<213> ORGANISM: Artificial
<220> FEATURE:
<223> OTHER INFORMATION: Target Sequence
```

<400> SEQUENCE: 62
acaaaggaac ctacttgta                                                        19

<210> SEQ ID NO 63
<211> LENGTH: 19
<212> TYPE: DNA
<213> ORGANISM: Artificial
<220> FEATURE:
<223> OTHER INFORMATION: Target Sequence

<400> SEQUENCE: 63
gaacctactt gtacaatga                                                        19

<210> SEQ ID NO 64
<211> LENGTH: 19
<212> TYPE: DNA
<213> ORGANISM: Artificial
<220> FEATURE:
<223> OTHER INFORMATION: Target Sequence

<400> SEQUENCE: 64
ctacttgtac aatgactgt                                                        19

<210> SEQ ID NO 65
<211> LENGTH: 19
<212> TYPE: DNA
<213> ORGANISM: Artificial
<220> FEATURE:
<223> OTHER INFORMATION: Target Sequence

<400> SEQUENCE: 65
tgtgagagcg gctccttca                                                        19

<210> SEQ ID NO 66
<211> LENGTH: 19
<212> TYPE: DNA
<213> ORGANISM: Artificial
<220> FEATURE:
<223> OTHER INFORMATION: Target Sequence

<400> SEQUENCE: 66
tcaggtggag atctcttct                                                        19

<210> SEQ ID NO 67
<211> LENGTH: 19
<212> TYPE: DNA
<213> ORGANISM: Artificial
<220> FEATURE:
<223> OTHER INFORMATION: Target Sequence

<400> SEQUENCE: 67
caggtggaga tctcttctt                                                        19

<210> SEQ ID NO 68
<211> LENGTH: 19
<212> TYPE: DNA
<213> ORGANISM: Artificial
<220> FEATURE:
<223> OTHER INFORMATION: Target Sequence

<400> SEQUENCE: 68
agaaccagta ccggcatta                                                        19

<210> SEQ ID NO 69
<211> LENGTH: 19
<212> TYPE: DNA

```
<213> ORGANISM: Artificial
<220> FEATURE:
<223> OTHER INFORMATION: Target Sequence

<400> SEQUENCE: 69
gaaccagtac cggcattat                                               19

<210> SEQ ID NO 70
<211> LENGTH: 19
<212> TYPE: DNA
<213> ORGANISM: Artificial
<220> FEATURE:
<223> OTHER INFORMATION: Target Sequence

<400> SEQUENCE: 70
aaccagtacc ggcattatt                                               19

<210> SEQ ID NO 71
<211> LENGTH: 19
<212> TYPE: DNA
<213> ORGANISM: Artificial
<220> FEATURE:
<223> OTHER INFORMATION: Target Sequence

<400> SEQUENCE: 71
ccggcattat tggagtgaa                                               19

<210> SEQ ID NO 72
<211> LENGTH: 19
<212> TYPE: DNA
<213> ORGANISM: Artificial
<220> FEATURE:
<223> OTHER INFORMATION: Target Sequence

<400> SEQUENCE: 72
cggcattatt ggagtgaaa                                               19

<210> SEQ ID NO 73
<211> LENGTH: 19
<212> TYPE: DNA
<213> ORGANISM: Artificial
<220> FEATURE:
<223> OTHER INFORMATION: Target Sequence

<400> SEQUENCE: 73
agcctggagt gcacgaagt                                               19

<210> SEQ ID NO 74
<211> LENGTH: 19
<212> TYPE: DNA
<213> ORGANISM: Artificial
<220> FEATURE:
<223> OTHER INFORMATION: Target Sequence

<400> SEQUENCE: 74
ctcctcttca ttggtttaa                                               19

<210> SEQ ID NO 75
<211> LENGTH: 19
<212> TYPE: DNA
<213> ORGANISM: Artificial
<220> FEATURE:
<223> OTHER INFORMATION: Target Sequence

<400> SEQUENCE: 75
ttggtttaat gtatcgcta                                               19
```

```
<210> SEQ ID NO 76
<211> LENGTH: 19
<212> TYPE: DNA
<213> ORGANISM: Artificial
<220> FEATURE:
<223> OTHER INFORMATION: Target Sequence

<400> SEQUENCE: 76
gtttaatgta tcgctacca                                              19

<210> SEQ ID NO 77
<211> LENGTH: 19
<212> TYPE: DNA
<213> ORGANISM: Artificial
<220> FEATURE:
<223> OTHER INFORMATION: Target Sequence

<400> SEQUENCE: 77
tttaatgtat cgctaccaa                                              19

<210> SEQ ID NO 78
<211> LENGTH: 19
<212> TYPE: DNA
<213> ORGANISM: Artificial
<220> FEATURE:
<223> OTHER INFORMATION: Target Sequence

<400> SEQUENCE: 78
agtccaagct ctactccat                                              19

<210> SEQ ID NO 79
<211> LENGTH: 19
<212> TYPE: DNA
<213> ORGANISM: Artificial
<220> FEATURE:
<223> OTHER INFORMATION: Target Sequence

<400> SEQUENCE: 79
gagcttgaag gaactacta                                              19

<210> SEQ ID NO 80
<211> LENGTH: 19
<212> TYPE: DNA
<213> ORGANISM: Artificial
<220> FEATURE:
<223> OTHER INFORMATION: Target Sequence

<400> SEQUENCE: 80
cttgaaggaa ctactacta                                              19

<210> SEQ ID NO 81
<211> LENGTH: 19
<212> TYPE: DNA
<213> ORGANISM: Artificial
<220> FEATURE:
<223> OTHER INFORMATION: Target Sequence

<400> SEQUENCE: 81
ttgaaggaac tactactaa                                              19

<210> SEQ ID NO 82
<211> LENGTH: 19
<212> TYPE: DNA
<213> ORGANISM: Artificial
<220> FEATURE:
<223> OTHER INFORMATION: Target Sequence
```

```
<400> SEQUENCE: 82
acaagccaca gagcctaga                                                 19

<210> SEQ ID NO 83
<211> LENGTH: 19
<212> TYPE: DNA
<213> ORGANISM: Artificial
<220> FEATURE:
<223> OTHER INFORMATION: Target Sequence

<400> SEQUENCE: 83
tgtacgccgt ggtggagaa                                                 19

<210> SEQ ID NO 84
<211> LENGTH: 19
<212> TYPE: DNA
<213> ORGANISM: Artificial
<220> FEATURE:
<223> OTHER INFORMATION: Target Sequence

<400> SEQUENCE: 84
ccgttgcgct ggaaggaat                                                 19

<210> SEQ ID NO 85
<211> LENGTH: 19
<212> TYPE: DNA
<213> ORGANISM: Artificial
<220> FEATURE:
<223> OTHER INFORMATION: Target Sequence

<400> SEQUENCE: 85
tctaaggacc gtcctgcga                                                 19

<210> SEQ ID NO 86
<211> LENGTH: 19
<212> TYPE: DNA
<213> ORGANISM: Artificial
<220> FEATURE:
<223> OTHER INFORMATION: Target Sequence

<400> SEQUENCE: 86
ctaatagaaa cttggcact                                                 19

<210> SEQ ID NO 87
<211> LENGTH: 19
<212> TYPE: DNA
<213> ORGANISM: Artificial
<220> FEATURE:
<223> OTHER INFORMATION: Target Sequence

<400> SEQUENCE: 87
taatagaaac ttggcactc                                                 19

<210> SEQ ID NO 88
<211> LENGTH: 19
<212> TYPE: DNA
<213> ORGANISM: Artificial
<220> FEATURE:
<223> OTHER INFORMATION: Target Sequence

<400> SEQUENCE: 88
aatagaaact tggcactcc                                                 19

<210> SEQ ID NO 89
<211> LENGTH: 19
<212> TYPE: DNA
```

<213> ORGANISM: Artificial
<220> FEATURE:
<223> OTHER INFORMATION: Target Sequence

<400> SEQUENCE: 89
atagaaactt ggcactcct                                              19

<210> SEQ ID NO 90
<211> LENGTH: 19
<212> TYPE: DNA
<213> ORGANISM: Artificial
<220> FEATURE:
<223> OTHER INFORMATION: Target Sequence

<400> SEQUENCE: 90
tagaaacttg gcactcctg                                              19

<210> SEQ ID NO 91
<211> LENGTH: 19
<212> TYPE: DNA
<213> ORGANISM: Artificial
<220> FEATURE:
<223> OTHER INFORMATION: Target Sequence

<400> SEQUENCE: 91
atagcaagct gaactgtcc                                              19

<210> SEQ ID NO 92
<211> LENGTH: 19
<212> TYPE: DNA
<213> ORGANISM: Artificial
<220> FEATURE:
<223> OTHER INFORMATION: Target Sequence

<400> SEQUENCE: 92
tagcaagctg aactgtcct                                              19

<210> SEQ ID NO 93
<211> LENGTH: 19
<212> TYPE: DNA
<213> ORGANISM: Artificial
<220> FEATURE:
<223> OTHER INFORMATION: Target Sequence

<400> SEQUENCE: 93
agcaagctga actgtccta                                              19

<210> SEQ ID NO 94
<211> LENGTH: 19
<212> TYPE: DNA
<213> ORGANISM: Artificial
<220> FEATURE:
<223> OTHER INFORMATION: Target Sequence

<400> SEQUENCE: 94
gcaagctgaa ctgtcctaa                                              19

<210> SEQ ID NO 95
<211> LENGTH: 19
<212> TYPE: DNA
<213> ORGANISM: Artificial
<220> FEATURE:
<223> OTHER INFORMATION: Target Sequence

<400> SEQUENCE: 95
tgaactgtcc taaggcagg                                              19

```
<210> SEQ ID NO 96
<211> LENGTH: 19
<212> TYPE: DNA
<213> ORGANISM: Artificial
<220> FEATURE:
<223> OTHER INFORMATION: Target Sequence

<400> SEQUENCE: 96
caaaggaacc tacttgtac                                                    19

<210> SEQ ID NO 97
<211> LENGTH: 19
<212> TYPE: DNA
<213> ORGANISM: Artificial
<220> FEATURE:
<223> OTHER INFORMATION: Target Sequence

<400> SEQUENCE: 97
gagcttgaag gaactacta                                                    19

<210> SEQ ID NO 98
<211> LENGTH: 19
<212> TYPE: DNA
<213> ORGANISM: Artificial
<220> FEATURE:
<223> OTHER INFORMATION: Target Sequence

<400> SEQUENCE: 98
cacagagcct agacactga                                                    19

<210> SEQ ID NO 99
<211> LENGTH: 19
<212> TYPE: DNA
<213> ORGANISM: Artificial
<220> FEATURE:
<223> OTHER INFORMATION: Target Sequence

<400> SEQUENCE: 99
tccaagctct actccattg                                                    19

<210> SEQ ID NO 100
<211> LENGTH: 19
<212> TYPE: DNA
<213> ORGANISM: Artificial
<220> FEATURE:
<223> OTHER INFORMATION: Target Sequence

<400> SEQUENCE: 100
tggagctgtt ggtgggaat                                                    19

<210> SEQ ID NO 101
<211> LENGTH: 19
<212> TYPE: DNA
<213> ORGANISM: Artificial
<220> FEATURE:
<223> OTHER INFORMATION: Target Sequence

<400> SEQUENCE: 101
gacagggaga agagagata                                                    19

<210> SEQ ID NO 102
<211> LENGTH: 19
<212> TYPE: DNA
<213> ORGANISM: Artificial
<220> FEATURE:
<223> OTHER INFORMATION: Target Sequence
```

-continued

```
<400> SEQUENCE: 102
gggagaagag agatagtgt                                                    19

<210> SEQ ID NO 103
<211> LENGTH: 19
<212> TYPE: DNA
<213> ORGANISM: Artificial
<220> FEATURE:
<223> OTHER INFORMATION: Target Sequence

<400> SEQUENCE: 103
gagaagagag atagtgtgt                                                    19

<210> SEQ ID NO 104
<211> LENGTH: 19
<212> TYPE: DNA
<213> ORGANISM: Artificial
<220> FEATURE:
<223> OTHER INFORMATION: Target Sequence

<400> SEQUENCE: 104
gaagagagat agtgtgtgt                                                    19

<210> SEQ ID NO 105
<211> LENGTH: 19
<212> TYPE: DNA
<213> ORGANISM: Artificial
<220> FEATURE:
<223> OTHER INFORMATION: Target Sequence

<400> SEQUENCE: 105
gtgtgtgtcc ccaaggaaa                                                    19

<210> SEQ ID NO 106
<211> LENGTH: 19
<212> TYPE: DNA
<213> ORGANISM: Artificial
<220> FEATURE:
<223> OTHER INFORMATION: Target Sequence

<400> SEQUENCE: 106
gaaaatatat ccaccctca                                                    19

<210> SEQ ID NO 107
<211> LENGTH: 19
<212> TYPE: DNA
<213> ORGANISM: Artificial
<220> FEATURE:
<223> OTHER INFORMATION: Target Sequence

<400> SEQUENCE: 107
aaatatatcc accctcaaa                                                    19

<210> SEQ ID NO 108
<211> LENGTH: 19
<212> TYPE: DNA
<213> ORGANISM: Artificial
<220> FEATURE:
<223> OTHER INFORMATION: Target Sequence

<400> SEQUENCE: 108
ctgtaccaag tgccacaaa                                                    19

<210> SEQ ID NO 109
<211> LENGTH: 19
<212> TYPE: DNA
```

```
<213> ORGANISM: Artificial
<220> FEATURE:
<223> OTHER INFORMATION: Target Sequence

<400> SEQUENCE: 109
accaagtgcc acaaaggaa                                                19

<210> SEQ ID NO 110
<211> LENGTH: 19
<212> TYPE: DNA
<213> ORGANISM: Artificial
<220> FEATURE:
<223> OTHER INFORMATION: Target Sequence

<400> SEQUENCE: 110 ccaagtgccacaaaggaac                                                 19

<210> SEQ ID NO 111
<211> LENGTH: 19
<212> TYPE: DNA
<213> ORGANISM: Artificial
<220> FEATURE:
<223> OTHER INFORMATION: Target Sequence

<400> SEQUENCE: 111 ccacaaaggaacctacttg                                                 19

<210> SEQ ID NO 112
<211> LENGTH: 19
<212> TYPE: DNA
<213> ORGANISM: Artificial
<220> FEATURE:
<223> OTHER INFORMATION: Target Sequence

<400> SEQUENCE: 112
caaaggaacc tacttgtac                                                19

<210> SEQ ID NO 113
<211> LENGTH: 19
<212> TYPE: DNA
<213> ORGANISM: Artificial
<220> FEATURE:
<223> OTHER INFORMATION: Target Sequence

<400> SEQUENCE: 113
aaaggaacct acttgtaca                                                19

<210> SEQ ID NO 114
<211> LENGTH: 19
<212> TYPE: DNA
<213> ORGANISM: Artificial
<220> FEATURE:
<223> OTHER INFORMATION: Target Sequence

<400> SEQUENCE: 114
gatacggact gcagggagt                                                19

<210> SEQ ID NO 115
<211> LENGTH: 19
<212> TYPE: DNA
<213> ORGANISM: Artificial
<220> FEATURE:
<223> OTHER INFORMATION: Target Sequence

<400> SEQUENCE: 115
cggactgcag ggagtgtga                                                19
```

```
<210> SEQ ID NO 116
<211> LENGTH: 19
<212> TYPE: DNA
<213> ORGANISM: Artificial
<220> FEATURE:
<223> OTHER INFORMATION: Target Sequence

<400> SEQUENCE: 116
tccttcaccg cttcagaaa                                                  19

<210> SEQ ID NO 117
<211> LENGTH: 19
<212> TYPE: DNA
<213> ORGANISM: Artificial
<220> FEATURE:
<223> OTHER INFORMATION: Target Sequence

<400> SEQUENCE: 117
cagaaaacca cctcagaca                                                  19

<210> SEQ ID NO 118
<211> LENGTH: 19
<212> TYPE: DNA
<213> ORGANISM: Artificial
<220> FEATURE:
<223> OTHER INFORMATION: Target Sequence

<400> SEQUENCE: 118
tgcctcagct gctccaaat                                                  19

<210> SEQ ID NO 119
<211> LENGTH: 19
<212> TYPE: DNA
<213> ORGANISM: Artificial
<220> FEATURE:
<223> OTHER INFORMATION: Target Sequence

<400> SEQUENCE: 119
ctccaaatgc cgaaaggaa                                                  19

<210> SEQ ID NO 120
<211> LENGTH: 19
<212> TYPE: DNA
<213> ORGANISM: Artificial
<220> FEATURE:
<223> OTHER INFORMATION: Target Sequence

<400> SEQUENCE: 120 tccaaatgccgaaaggaaa                                                   19

<210> SEQ ID NO 121
<211> LENGTH: 19
<212> TYPE: DNA
<213> ORGANISM: Artificial
<220> FEATURE:
<223> OTHER INFORMATION: Target Sequence

<400> SEQUENCE: 121
ccaaatgccg aaaggaaat                                                  19

<210> SEQ ID NO 122
<211> LENGTH: 19
<212> TYPE: DNA
<213> ORGANISM: Artificial
<220> FEATURE:
<223> OTHER INFORMATION: Target Sequence
```

```
<400> SEQUENCE: 122
gccgaaagga aatgggtca                                              19

<210> SEQ ID NO 123
<211> LENGTH: 19
<212> TYPE: DNA
<213> ORGANISM: Artificial
<220> FEATURE:
<223> OTHER INFORMATION: Target Sequence

<400> SEQUENCE: 123
aggaaatggg tcaggtgga                                              19

<210> SEQ ID NO 124
<211> LENGTH: 19
<212> TYPE: DNA
<213> ORGANISM: Artificial
<220> FEATURE:
<223> OTHER INFORMATION: Target Sequence

<400> SEQUENCE: 124
ggaaatgggt caggtggag                                              19

<210> SEQ ID NO 125
<211> LENGTH: 19
<212> TYPE: DNA
<213> ORGANISM: Artificial
<220> FEATURE:
<223> OTHER INFORMATION: Target Sequence

<400> SEQUENCE: 125
gtgtgtggct gcaggaaga                                              19

<210> SEQ ID NO 126
<211> LENGTH: 19
<212> TYPE: DNA
<213> ORGANISM: Artificial
<220> FEATURE:
<223> OTHER INFORMATION: Target Sequence

<400> SEQUENCE: 126
ggaagaacca gtaccggca                                              19

<210> SEQ ID NO 127
<211> LENGTH: 19
<212> TYPE: DNA
<213> ORGANISM: Artificial
<220> FEATURE:
<223> OTHER INFORMATION: Target Sequence

<400> SEQUENCE: 127
ccatgcaggt ttctttcta                                              19

<210> SEQ ID NO 128
<211> LENGTH: 19
<212> TYPE: DNA
<213> ORGANISM: Artificial
<220> FEATURE:
<223> OTHER INFORMATION: Target Sequence

<400> SEQUENCE: 128
catgcaggtt tctttctaa                                              19

<210> SEQ ID NO 129
<211> LENGTH: 19
<212> TYPE: DNA
```

-continued

<213> ORGANISM: Artificial
<220> FEATURE:
<223> OTHER INFORMATION: Target Sequence

<400> SEQUENCE: 129
tgcaggtttc tttctaaga                                               19

<210> SEQ ID NO 130
<211> LENGTH: 19
<212> TYPE: DNA
<213> ORGANISM: Artificial
<220> FEATURE:
<223> OTHER INFORMATION: Target Sequence

<400> SEQUENCE: 130
aggtttcttt ctaagagaa                                               19

<210> SEQ ID NO 131
<211> LENGTH: 19
<212> TYPE: DNA
<213> ORGANISM: Artificial
<220> FEATURE:
<223> OTHER INFORMATION: Target Sequence

<400> SEQUENCE: 131
ggtttctttc taagagaaa                                               19

<210> SEQ ID NO 132
<211> LENGTH: 19
<212> TYPE: DNA
<213> ORGANISM: Artificial
<220> FEATURE:
<223> OTHER INFORMATION: Target Sequence

<400> SEQUENCE: 132
agagaaaacg agtgtgtct                                               19

<210> SEQ ID NO 133
<211> LENGTH: 19
<212> TYPE: DNA
<213> ORGANISM: Artificial
<220> FEATURE:
<223> OTHER INFORMATION: Target Sequence

<400> SEQUENCE: 133
gagtgtgtct cctgtagta                                               19

<210> SEQ ID NO 134
<211> LENGTH: 19
<212> TYPE: DNA
<213> ORGANISM: Artificial
<220> FEATURE:
<223> OTHER INFORMATION: Target Sequence

<400> SEQUENCE: 134
ctgtagtaac tgtaagaaa                                               19

<210> SEQ ID NO 135
<211> LENGTH: 19
<212> TYPE: DNA
<213> ORGANISM: Artificial
<220> FEATURE:
<223> OTHER INFORMATION: Target Sequence

<400> SEQUENCE: 135
agaaaagcct ggagtgcac                                               19

```
<210> SEQ ID NO 136
<211> LENGTH: 19
<212> TYPE: DNA
<213> ORGANISM: Artificial
<220> FEATURE:
<223> OTHER INFORMATION: Target Sequence

<400> SEQUENCE: 136
ttgagaatgt taagggcac                                               19

<210> SEQ ID NO 137
<211> LENGTH: 19
<212> TYPE: DNA
<213> ORGANISM: Artificial
<220> FEATURE:
<223> OTHER INFORMATION: Target Sequence

<400> SEQUENCE: 137
tgttaagggc actgaggac                                               19

<210> SEQ ID NO 138
<211> LENGTH: 19
<212> TYPE: DNA
<213> ORGANISM: Artificial
<220> FEATURE:
<223> OTHER INFORMATION: Target Sequence

<400> SEQUENCE: 138
ggtcattttc tttggtctt                                               19

<210> SEQ ID NO 139
<211> LENGTH: 19
<212> TYPE: DNA
<213> ORGANISM: Artificial
<220> FEATURE:
<223> OTHER INFORMATION: Target Sequence

<400> SEQUENCE: 139
cctcctcttc attggttta                                               19

<210> SEQ ID NO 140
<211> LENGTH: 19
<212> TYPE: DNA
<213> ORGANISM: Artificial
<220> FEATURE:
<223> OTHER INFORMATION: Target Sequence

<400> SEQUENCE: 140
tcctcttcat tggtttaat                                               19

<210> SEQ ID NO 141
<211> LENGTH: 19
<212> TYPE: DNA
<213> ORGANISM: Artificial
<220> FEATURE:
<223> OTHER INFORMATION: Target Sequence

<400> SEQUENCE: 141
ctcttcattg gtttaatgt                                               19

<210> SEQ ID NO 142
<211> LENGTH: 19
<212> TYPE: DNA
<213> ORGANISM: Artificial
<220> FEATURE:
<223> OTHER INFORMATION: Target Sequence
```

```
<400> SEQUENCE: 142
tcttcattgg tttaatgta                                              19

<210> SEQ ID NO 143
<211> LENGTH: 19
<212> TYPE: DNA
<213> ORGANISM: Artificial
<220> FEATURE:
<223> OTHER INFORMATION: Target Sequence

<400> SEQUENCE: 143
cttcattggt ttaatgtat                                              19

<210> SEQ ID NO 144
<211> LENGTH: 19
<212> TYPE: DNA
<213> ORGANISM: Artificial
<220> FEATURE:
<223> OTHER INFORMATION: Target Sequence

<400> SEQUENCE: 144
tccaagctct actccattg                                              19

<210> SEQ ID NO 145
<211> LENGTH: 19
<212> TYPE: DNA
<213> ORGANISM: Artificial
<220> FEATURE:
<223> OTHER INFORMATION: Target Sequence

<400> SEQUENCE: 145
ctccattgtt tgtgggaaa                                              19

<210> SEQ ID NO 146
<211> LENGTH: 19
<212> TYPE: DNA
<213> ORGANISM: Artificial
<220> FEATURE:
<223> OTHER INFORMATION: Target Sequence

<400> SEQUENCE: 146
gggaaatcga cacctgaaa                                              19

<210> SEQ ID NO 147
<211> LENGTH: 19
<212> TYPE: DNA
<213> ORGANISM: Artificial
<220> FEATURE:
<223> OTHER INFORMATION: Target Sequence

<400> SEQUENCE: 147
tgaaggaact actactaag                                              19

<210> SEQ ID NO 148
<211> LENGTH: 19
<212> TYPE: DNA
<213> ORGANISM: Artificial
<220> FEATURE:
<223> OTHER INFORMATION: Target Sequence

<400> SEQUENCE: 148
acctccagct ccacctata                                              19

<210> SEQ ID NO 149
<211> LENGTH: 19
<212> TYPE: DNA
```

-continued

<213> ORGANISM: Artificial
<220> FEATURE:
<223> OTHER INFORMATION: Target Sequence

<400> SEQUENCE: 149
cccacaagcc acagagcct                                                 19

<210> SEQ ID NO 150
<211> LENGTH: 19
<212> TYPE: DNA
<213> ORGANISM: Artificial
<220> FEATURE:
<223> OTHER INFORMATION: Target Sequence

<400> SEQUENCE: 150
acgccgtggt ggagaacgt                                                 19

<210> SEQ ID NO 151
<211> LENGTH: 19
<212> TYPE: DNA
<213> ORGANISM: Artificial
<220> FEATURE:
<223> OTHER INFORMATION: Target Sequence

<400> SEQUENCE: 151
ggaaggaatt cgtgcggcg                                                 19

<210> SEQ ID NO 152
<211> LENGTH: 19
<212> TYPE: DNA
<213> ORGANISM: Artificial
<220> FEATURE:
<223> OTHER INFORMATION: Target Sequence

<400> SEQUENCE: 152
tgagcgacca cgagatcga                                                 19

<210> SEQ ID NO 153
<211> LENGTH: 19
<212> TYPE: DNA
<213> ORGANISM: Artificial
<220> FEATURE:
<223> OTHER INFORMATION: Target Sequence

<400> SEQUENCE: 153
gcgaggcgca atacagcat                                                 19

<210> SEQ ID NO 154
<211> LENGTH: 19
<212> TYPE: DNA
<213> ORGANISM: Artificial
<220> FEATURE:
<223> OTHER INFORMATION: Target Sequence

<400> SEQUENCE: 154
tgggctgcct ggaggacat                                                 19

<210> SEQ ID NO 155
<211> LENGTH: 19
<212> TYPE: DNA
<213> ORGANISM: Artificial
<220> FEATURE:
<223> OTHER INFORMATION: Target Sequence

<400> SEQUENCE: 155
catcaagtac tgaacgttt                                                 19

```
<210> SEQ ID NO 156
<211> LENGTH: 19
<212> TYPE: DNA
<213> ORGANISM: Artificial
<220> FEATURE:
<223> OTHER INFORMATION: Target Sequence

<400> SEQUENCE: 156
tcgtggtggt ggatggtaa                                                   19

<210> SEQ ID NO 157
<211> LENGTH: 19
<212> TYPE: DNA
<213> ORGANISM: Artificial
<220> FEATURE:
<223> OTHER INFORMATION: Target Sequence

<400> SEQUENCE: 157
gaaagcgagt acactgtaa                                                   19

<210> SEQ ID NO 158
<211> LENGTH: 19
<212> TYPE: DNA
<213> ORGANISM: Artificial
<220> FEATURE:
<223> OTHER INFORMATION: Target Sequence

<400> SEQUENCE: 158
gagcctgact ctagggttc                                                   19

<210> SEQ ID NO 159
<211> LENGTH: 19
<212> TYPE: DNA
<213> ORGANISM: Artificial
<220> FEATURE:
<223> OTHER INFORMATION: Target Sequence

<400> SEQUENCE: 159
ccacataaga gatgatgat                                                   19

<210> SEQ ID NO 160
<211> LENGTH: 19
<212> TYPE: DNA
<213> ORGANISM: Artificial
<220> FEATURE:
<223> OTHER INFORMATION: Target Sequence

<400> SEQUENCE: 160
cataagagat gatgatgtt                                                   19

<210> SEQ ID NO 161
<211> LENGTH: 19
<212> TYPE: DNA
<213> ORGANISM: Artificial
<220> FEATURE:
<223> OTHER INFORMATION: Target Sequence

<400> SEQUENCE: 161
cgaatataac atagagcca                                                   19

<210> SEQ ID NO 162
<211> LENGTH: 19
<212> TYPE: DNA
<213> ORGANISM: Artificial
<220> FEATURE:
<223> OTHER INFORMATION: Target Sequence
```

<400> SEQUENCE: 162
gttaatgata ccaaagaca                                                19

<210> SEQ ID NO 163
<211> LENGTH: 19
<212> TYPE: DNA
<213> ORGANISM: Artificial
<220> FEATURE:
<223> OTHER INFORMATION: Target Sequence

<400> SEQUENCE: 163
ctgaagatat caagaatgt                                                19

<210> SEQ ID NO 164
<211> LENGTH: 19
<212> TYPE: DNA
<213> ORGANISM: Artificial
<220> FEATURE:
<223> OTHER INFORMATION: Target Sequence

<400> SEQUENCE: 164
atgaagagtt gctcccaaa                                                19

<210> SEQ ID NO 165
<211> LENGTH: 19
<212> TYPE: DNA
<213> ORGANISM: Artificial
<220> FEATURE:
<223> OTHER INFORMATION: Target Sequence

<400> SEQUENCE: 165
atgaagaaca cgtgtaaat                                                19

<210> SEQ ID NO 166
<211> LENGTH: 19
<212> TYPE: DNA
<213> ORGANISM: Artificial
<220> FEATURE:
<223> OTHER INFORMATION: Target Sequence

<400> SEQUENCE: 166
aattattggt ggtagcaga                                                19

<210> SEQ ID NO 167
<211> LENGTH: 19
<212> TYPE: DNA
<213> ORGANISM: Artificial
<220> FEATURE:
<223> OTHER INFORMATION: Target Sequence

<400> SEQUENCE: 167
atcatcgctt ctacagata                                                19

<210> SEQ ID NO 168
<211> LENGTH: 19
<212> TYPE: DNA
<213> ORGANISM: Artificial
<220> FEATURE:
<223> OTHER INFORMATION: Target Sequence

<400> SEQUENCE: 168
atacatgggc agaggggaa                                                19

<210> SEQ ID NO 169
<211> LENGTH: 19
<212> TYPE: DNA

```
<213> ORGANISM: Artificial
<220> FEATURE:
<223> OTHER INFORMATION: Target Sequence

<400> SEQUENCE: 169
gggcagaggg gaagagagt                                              19

<210> SEQ ID NO 170
<211> LENGTH: 19
<212> TYPE: DNA
<213> ORGANISM: Artificial
<220> FEATURE:
<223> OTHER INFORMATION: Target Sequence

<400> SEQUENCE: 170
ggaagagagt acaactaca                                              19

<210> SEQ ID NO 171
<211> LENGTH: 19
<212> TYPE: DNA
<213> ORGANISM: Artificial
<220> FEATURE:
<223> OTHER INFORMATION: Target Sequence

<400> SEQUENCE: 171
gaagagagta caactacaa                                              19

<210> SEQ ID NO 172
<211> LENGTH: 19
<212> TYPE: DNA
<213> ORGANISM: Artificial
<220> FEATURE:
<223> OTHER INFORMATION: Target Sequence

<400> SEQUENCE: 172
gagagtacaa ctacaaatt                                              19

<210> SEQ ID NO 173
<211> LENGTH: 19
<212> TYPE: DNA
<213> ORGANISM: Artificial
<220> FEATURE:
<223> OTHER INFORMATION: Target Sequence

<400> SEQUENCE: 173
gctaattgac agagttgat                                              19

<210> SEQ ID NO 174
<211> LENGTH: 19
<212> TYPE: DNA
<213> ORGANISM: Artificial
<220> FEATURE:
<223> OTHER INFORMATION: Target Sequence

<400> SEQUENCE: 174
cggaacactt catgggata                                              19

<210> SEQ ID NO 175
<211> LENGTH: 19
<212> TYPE: DNA
<213> ORGANISM: Artificial
<220> FEATURE:
<223> OTHER INFORMATION: Target Sequence

<400> SEQUENCE: 175
ggataatgca ggttttaaa                                              19
```

```
<210> SEQ ID NO 176
<211> LENGTH: 19
<212> TYPE: DNA
<213> ORGANISM: Artificial
<220> FEATURE:
<223> OTHER INFORMATION: Target Sequence

<400> SEQUENCE: 176
aggctatgga atacagata                                              19

<210> SEQ ID NO 177
<211> LENGTH: 19
<212> TYPE: DNA
<213> ORGANISM: Artificial
<220> FEATURE:
<223> OTHER INFORMATION: Target Sequence

<400> SEQUENCE: 177
gaatacagat agagcagat                                              19

<210> SEQ ID NO 178
<211> LENGTH: 19
<212> TYPE: DNA
<213> ORGANISM: Artificial
<220> FEATURE:
<223> OTHER INFORMATION: Target Sequence

<400> SEQUENCE: 178
ggtaaaacct ggtgaaaag                                              19

<210> SEQ ID NO 179
<211> LENGTH: 19
<212> TYPE: DNA
<213> ORGANISM: Artificial
<220> FEATURE:
<223> OTHER INFORMATION: Target Sequence

<400> SEQUENCE: 179
gtgaaaagca ctacaacat                                              19

<210> SEQ ID NO 180
<211> LENGTH: 19
<212> TYPE: DNA
<213> ORGANISM: Artificial
<220> FEATURE:
<223> OTHER INFORMATION: Target Sequence

<400> SEQUENCE: 180
gaggaagcat ctaaagttt                                              19

<210> SEQ ID NO 181
<211> LENGTH: 19
<212> TYPE: DNA
<213> ORGANISM: Artificial
<220> FEATURE:
<223> OTHER INFORMATION: Target Sequence

<400> SEQUENCE: 181
tatgggaact cttggatta                                              19

<210> SEQ ID NO 182
<211> LENGTH: 19
<212> TYPE: DNA
<213> ORGANISM: Artificial
<220> FEATURE:
<223> OTHER INFORMATION: Target Sequence
```

```
<400> SEQUENCE: 182
tgacgagcac aaagaatta                                               19

<210> SEQ ID NO 183
<211> LENGTH: 19
<212> TYPE: DNA
<213> ORGANISM: Artificial
<220> FEATURE:
<223> OTHER INFORMATION: Target Sequence

<400> SEQUENCE: 183
gcacaaagaa ttatggtaa                                               19

<210> SEQ ID NO 184
<211> LENGTH: 19
<212> TYPE: DNA
<213> ORGANISM: Artificial
<220> FEATURE:
<223> OTHER INFORMATION: Target Sequence

<400> SEQUENCE: 184
ggttacaact catgaattg                                               19

<210> SEQ ID NO 185
<211> LENGTH: 19
<212> TYPE: DNA
<213> ORGANISM: Artificial
<220> FEATURE:
<223> OTHER INFORMATION: Target Sequence

<400> SEQUENCE: 185
actcatgaat tgggacata                                               19

<210> SEQ ID NO 186
<211> LENGTH: 19
<212> TYPE: DNA
<213> ORGANISM: Artificial
<220> FEATURE:
<223> OTHER INFORMATION: Target Sequence

<400> SEQUENCE: 186
gtggcgatca cgagaacaa                                               19

<210> SEQ ID NO 187
<211> LENGTH: 19
<212> TYPE: DNA
<213> ORGANISM: Artificial
<220> FEATURE:
<223> OTHER INFORMATION: Target Sequence

<400> SEQUENCE: 187
ctataagacc attgaaagt                                               19

<210> SEQ ID NO 188
<211> LENGTH: 19
<212> TYPE: DNA
<213> ORGANISM: Artificial
<220> FEATURE:
<223> OTHER INFORMATION: Target Sequence

<400> SEQUENCE: 188
gaacgcagca ataaagttt                                               19

<210> SEQ ID NO 189
<211> LENGTH: 19
<212> TYPE: DNA
```

<213> ORGANISM: Artificial
<220> FEATURE:
<223> OTHER INFORMATION: Target Sequence

<400> SEQUENCE: 189
gcaataaagt ttgtgggaa                                                    19

<210> SEQ ID NO 190
<211> LENGTH: 19
<212> TYPE: DNA
<213> ORGANISM: Artificial
<220> FEATURE:
<223> OTHER INFORMATION: Target Sequence

<400> SEQUENCE: 190
caataaagtt tgtgggaac                                                    19

<210> SEQ ID NO 191
<211> LENGTH: 19
<212> TYPE: DNA
<213> ORGANISM: Artificial
<220> FEATURE:
<223> OTHER INFORMATION: Target Sequence

<400> SEQUENCE: 191
gagggtggat gaaggagaa                                                    19

<210> SEQ ID NO 192
<211> LENGTH: 19
<212> TYPE: DNA
<213> ORGANISM: Artificial
<220> FEATURE:
<223> OTHER INFORMATION: Target Sequence

<400> SEQUENCE: 192
ggatgaagga gaagagtgt                                                    19

<210> SEQ ID NO 193
<211> LENGTH: 19
<212> TYPE: DNA
<213> ORGANISM: Artificial
<220> FEATURE:
<223> OTHER INFORMATION: Target Sequence

<400> SEQUENCE: 193
gcatcatgta tctgaacaa                                                    19

<210> SEQ ID NO 194
<211> LENGTH: 19
<212> TYPE: DNA
<213> ORGANISM: Artificial
<220> FEATURE:
<223> OTHER INFORMATION: Target Sequence

<400> SEQUENCE: 194
caggaaatgc tgaagatga                                                    19

<210> SEQ ID NO 195
<211> LENGTH: 19
<212> TYPE: DNA
<213> ORGANISM: Artificial
<220> FEATURE:
<223> OTHER INFORMATION: Target Sequence

<400> SEQUENCE: 195
gaatggcaaa tgtgagaaa                                                    19

-continued

```
<210> SEQ ID NO 196
<211> LENGTH: 19
<212> TYPE: DNA
<213> ORGANISM: Artificial
<220> FEATURE:
<223> OTHER INFORMATION: Target Sequence

<400> SEQUENCE: 196
ggatgtaatt gaacgattt                                                   19

<210> SEQ ID NO 197
<211> LENGTH: 19
<212> TYPE: DNA
<213> ORGANISM: Artificial
<220> FEATURE:
<223> OTHER INFORMATION: Target Sequence

<400> SEQUENCE: 197
gtggataaga aattggata                                                   19

<210> SEQ ID NO 198
<211> LENGTH: 19
<212> TYPE: DNA
<213> ORGANISM: Artificial
<220> FEATURE:
<223> OTHER INFORMATION: Target Sequence

<400> SEQUENCE: 198
ggataaacag tatgaatct                                                   19

<210> SEQ ID NO 199
<211> LENGTH: 19
<212> TYPE: DNA
<213> ORGANISM: Artificial
<220> FEATURE:
<223> OTHER INFORMATION: Target Sequence

<400> SEQUENCE: 199
cctttaaact gcagcgtca                                                   19

<210> SEQ ID NO 200
<211> LENGTH: 19
<212> TYPE: DNA
<213> ORGANISM: Artificial
<220> FEATURE:
<223> OTHER INFORMATION: Target Sequence

<400> SEQUENCE: 200
cgtgttgaca gcaaagaaa                                                   19

<210> SEQ ID NO 201
<211> LENGTH: 19
<212> TYPE: DNA
<213> ORGANISM: Artificial
<220> FEATURE:
<223> OTHER INFORMATION: Target Sequence

<400> SEQUENCE: 201
gcaaagaaac agagtgcta                                                   19

<210> SEQ ID NO 202
<211> LENGTH: 19
<212> TYPE: RNA
<213> ORGANISM: Artificial
<220> FEATURE:
<223> OTHER INFORMATION: Target Sequence
```

```
<400> SEQUENCE: 202
caaaggaacc uacuuguac                                                19

<210> SEQ ID NO 203
<211> LENGTH: 19
<212> TYPE: RNA
<213> ORGANISM: Artificial
<220> FEATURE:
<223> OTHER INFORMATION: Target Sequence

<400> SEQUENCE: 203
gagcuugaag gaacuacua                                                19

<210> SEQ ID NO 204
<211> LENGTH: 19
<212> TYPE: RNA
<213> ORGANISM: Artificial
<220> FEATURE:
<223> OTHER INFORMATION: Target Sequence

<400> SEQUENCE: 204
cacagagccu agacacuga                                                19

<210> SEQ ID NO 205
<211> LENGTH: 19
<212> TYPE: RNA
<213> ORGANISM: Artificial
<220> FEATURE:
<223> OTHER INFORMATION: Target Sequence

<400> SEQUENCE: 205
uccaagcucu acuccauug                                                19
```

RNAI-MEDIATED INHIBITION OF TUMOR NECROSIS FACTOR α-RELATED CONDITIONS

RELATED APPLICATION

The present application is a divisional application of U.S. patent application Ser. No. 12/700,188 filed Feb. 4, 2010 (now abandoned), which claims benefit to U.S. patent application Ser. No. 11/750,262 filed May 17, 2007 (now U.S. Pat. No. 7,732,421), which claims benefit to U.S. Provisional Patent Application Ser. No. 60/801,788 filed on May, 19, 2006, titled RNAi-MEDIATED INHIBITION OF TUMOR NECROSIS FACTOR α-RELATED CONDITIONS, the text of which is specifically incorporated by reference herein.

FIELD OF THE INVENTION

The present invention relates to the field of interfering RNA compositions for silencing tumor necrosis factor α (TNFα) by silencing the TNFα cell surface receptor TNF receptor-1 (TNFR1) mRNA, or the TNFα converting enzyme (TACE/ADAM17) mRNA. Silencing such TNFα targets is useful for treatment of patients having a TNFα-related condition or at risk of developing such a condition.

BACKGROUND OF THE INVENTION

Inflammation is generally treated with a standard anti-inflammatory regimen that includes steroids and/or non-steroidal anti-inflammatory drugs (NSAIDS). Allergic conjunctivitis, ocular inflammation, dermatitis, rhinitis, and asthma have historically been treated with a regimen of oral, intranasal or topical antihistamines in addition to or oral or intranasal steroids. Systemic treatment typically requires higher concentrations of the drug compound to be administered to afford an effective concentration to reach the necessary treatment site. Antihistamine compounds are known to have central nervous system activity; drowsiness and drying of mucus membranes are a common side-effect of antihistamine use. Steroids and NSAIDS have potential side effects including intraocular pressure increase, cataract, glaucoma or corneal melting.

Dry eye, also known as conjunctivitis sicca or keratoconjunctivitis sicca, is a common ophthalmological disorder involving breakdown of the pre-ocular tear film, resulting in dehydration of the exposed outer surface of the eye. To date, dry eye has been treated with topical administration of artificial tear solutions. Some of these solutions contain mucomimetic substances to temporarily replace or replenish the mucin layer in mucin deficient patients. Use of methylprednisolone has been proposed in a short-term "pulse" treatment to treat exacerbations of dry eye. The proposed "pulse" therapy is required to avoid complications associated with traditional steroid therapy for inflammatory conditions such as increased intraocular pressure and cataract formation.

The cytokine TNFα is a target for anti-inflammatory therapy of dry eye and uveitis. In a rabbit model of lacrimal gland inflammation-induced dry eye, inhibition of corneal staining and restoration of tear breakup time has been achieved by specific modulation of ocular surface TNFα levels. Dry eye therapy resulted by inhibiting TNFα synthesis (RDP58) or by specifically neutralizing TNFα using a monoclonal antibody (REMICADE®) or a soluble receptor (ENBREL®). Each of these TNFα directed treatments resulted in levels of efficacy obtained with topical ocular anti-inflammatory steroids.

U.S. Patent Publication 2005/0227935, published Oct. 13, 2005, to McSwiggen et al. relates to RNA interference mediated inhibition of TNF and TNF receptor gene expression. However, said publication teaches none of the particular target sequences for RNA interference as provided herein.

Embodiments of the present invention address the need in the art for further agents and treatment methods for dry eye and inflammation and provide alternative therapies therefor.

SUMMARY OF THE INVENTION

Embodiments of the present invention provide highly potent and efficacious treatment, prevention or intervention of a TNFα-related condition without side effects associated with steroids or NSAIDS. In one aspect, methods of the invention include treating a subject having a TNFα-related condition or at risk of developing a TNFα-related condition by administering interfering RNAs that silence expression of TACE mRNA or TNFR1 mRNA, thus interfering with proteolytic processing of the precursor to TNFα, or interfering with binding of TNFα to its cell surface receptor, respectively, thereby attenuating activity of TNFα and preventing a cascade of events related to apoptosis and inflammation.

A TNFα-related condition includes conditions such as dry eye and TNFα-related inflammatory conditions. A TNFα-related inflammatory condition includes conditions such as ocular inflammation, allergic conjunctivitis, dermatitis, rhinitis, and asthma, for example, and includes those cellular changes resulting from the activity of TNFα that leads directly or indirectly to the TNFα-related inflammatory condition. A TNFα-related condition particularly includes TNFα-related ocular conditions such as dry eye, allergic conjunctivitis, and ocular inflammation. The interfering RNA provided herein provides for silencing the TNFα targets TACE mRNA or TNFR1 mRNA while avoiding undesirable side effects due to nonspecific agents.

A method of attenuating expression of TACE mRNA of the subject is an embodiment of the invention. The method comprises administering to the subject a composition comprising an effective amount of interfering RNA having a length of 19 to 49 nucleotides and a pharmaceutically acceptable carrier, the interfering RNA comprising a region of at least 13 contiguous nucleotides having at least 90% sequence complementarity to, or at least 90% sequence identity with, the penultimate 13 nucleotides of the 3' end of an mRNA corresponding to any one of SEQ ID NO:3, SEQ ID NO:14-SEQ ID NO:58, and SEQ ID NO:155-SEQ ID NO:201. The expression of TACE mRNA is attenuated thereby.

A method of treating a TNFα-related condition in a subject in need thereof is an embodiment of the invention. The method comprises administering to the subject a composition comprising an effective amount of interfering RNA having a length of 19 to 49 nucleotides, and a pharmaceutically acceptable carrier, wherein the interfering RNA comprises a region of at least 13 contiguous nucleotides having at least 90% sequence complementarity to, or at least 90% sequence identity with, the penultimate 13 nucleotides of the 3' end of an mRNA corresponding to any one of SEQ ID NO:3, SEQ ID NO:14-SEQ ID NO:58, and SEQ ID NO:155-SEQ ID NO:201. The TNFα-related condition is treated thereby.

In yet another embodiment of the invention, a method of attenuating activity of TNFα of a subject by attenuating expression of TACE mRNA or TNFR1 mRNA of the subject comprises administering to the subject a composition comprising an effective amount of interfering RNA having a length of 19 to 49 nucleotides and a pharmaceutically acceptable carrier and the interfering RNA comprises a sense nucleotide strand, an antisense nucleotide strand, and a region of at least near-perfect contiguous complementarity of at least 19 nucleotides where the antisense strand hybridizes under physiological conditions to a portion of mRNA corresponding to SEQ ID NO:1 comprising nucleotide 297, 333, 334, 335, 434, 470, 493, 547, 570, 573, 618, 649, 689, 755, 842, 844, 846, 860, 878, 894, 900, 909, 910, 913, 942, 970, 984, 1002, 1010, 1053, 1064, 1137, 1162, 1215, 1330, 1334, 1340, 1386, 1393, 1428, 1505, 1508, 1541, 1553, 1557, 1591, 1592, 1593, 1597, 1604, 1605, 1626, 1632, 1658, 1661, 1691, 1794, 1856, 1945, 1946, 1947, 1958, 2022, 2094, 2100, 2121, 2263, 2277, 2347, 2349, 2549, 2578, 2595, 2606, 2608, 2629, 2639, 2764, 2766, 2767, 2769, 3027, 3028, 3261, 3264, 3284, 3313, 3317, 3332, or 3337 or where the antisense strand hybridizes under physiological conditions to a portion of mRNA corresponding to SEQ ID NO:2 beginning at nucleotide 124, 328, 387, 391, 393, 395, 406, 421, 423, 444, 447, 455, 459, 460, 467, 469, 470, 471, 475, 479, 513, 517, 531, 543, 556, 576, 587, 588, 589, 595, 601, 602, 611, 612, 651, 664, 667, 668, 669, 677, 678, 785, 786, 788, 791, 792, 804, 813, 824, 838, 843, 877, 884, 929, 959, 960, 961, 963, 964, 965, 970, 973, 974, 1000, 1002, 1013, 1026, 1053, 1056, 1057, 1058, 1161, 1315, 1318, 1324, 1357, 1360, 1383, 1393, 1420, 1471, 1573, 1671, 2044, 2045, 2046, 2047, 2048, 2089, 2090, 2091, 2092, or 2098. The expression of TACE mRNA is attenuated in those embodiments where the antisense stand hybridizes to a portion of mRNA corresponding to SEQ ID NO:1 as cited above. The expression of TNFR1 mRNA is attenuated in those embodiments where the antisense stand hybridizes to a portion of mRNA corresponding to SEQ ID NO:2 as cited above.

A method of treating a TNFα-related condition in a subject in need thereof is an embodiment of the invention, the method comprising administering to the subject a composition comprising an effective amount of interfering RNA having a length of 19 to 49 nucleotides, and a pharmaceutically acceptable carrier, the interfering RNA comprising a sense nucleotide strand, an antisense nucleotide strand, and a region of at least near-perfect contiguous complementarity of at least 19 nucleotides; wherein the antisense strand hybridizes under physiological conditions to a portion of mRNA corresponding to SEQ ID NO:1 comprising nucleotide 297, 333, 334, 335, 434, 470, 493, 547, 570, 573, 618, 649, 689, 755, 842, 844, 846, 860, 878, 894, 900, 909, 910, 913, 942, 970, 984, 1002, 1010, 1053, 1064, 1137, 1162, 1215, 1330, 1334, 1340, 1386, 1393, 1428, 1505, 1508, 1541, 1553, 1557, 1591, 1592, 1593, 1597, 1604, 1605, 1626, 1632, 1658, 1661, 1691, 1794, 1856, 1945, 1946, 1947, 1958, 2022, 2094, 2100, 2121, 2263, 2277, 2347, 2349, 2549, 2578, 2595, 2606, 2608, 2629, 2639, 2764, 2766, 2767, 2769, 3027, 3028, 3261, 3264, 3284, 3313, 3317, 3332, or 3337. The TNFα-related condition is treated thereby.

A method of treating a TNFα-related ocular condition in a subject in need thereof is an embodiment of the invention, the method comprising administering to the subject a composition comprising an effective amount of interfering RNA having a length of 19 to 49 nucleotides, and a pharmaceutically acceptable carrier, the interfering RNA comprising a sense nucleotide strand, an antisense nucleotide strand, and a region of at least near-perfect contiguous complementarity of at least 19 nucleotides; wherein the antisense strand hybridizes under physiological conditions to a portion of mRNA corresponding to SEQ ID NO:2 comprising nucleotide 124, 328, 387, 391, 393, 395, 406, 421, 423, 444, 447, 455, 459, 460, 467, 469, 470, 471, 475, 479, 513, 517, 531, 543, 556, 576, 587, 588, 589, 595, 601, 602, 611, 612, 651, 664, 667, 668, 669, 677, 678, 785, 786, 788, 791, 792, 804, 813, 824, 838, 843, 877, 884, 929, 959, 960, 961, 963, 964, 965, 970, 973, 974, 1000, 1002, 1013, 1026, 1053, 1056, 1057, 1058, 1161, 1315, 1318, 1324, 1357, 1360, 1383, 1393, 1420, 1471, 1573, 1671, 2044, 2045, 2046, 2047, 2048, 2089, 2090, 2091, 2092, or 2098. The TNFα-related condition is treated thereby.

A second interfering RNA having a length of 19 to 49 nucleotides could also be administered to the subject in a further embodiment; the second interfering RNA comprising a sense nucleotide strand, an antisense nucleotide strand, and a region of at least near-perfect complementarity of at least 19 nucleotides wherein the antisense strand of the second interfering RNA hybridizes under physiological conditions to a portion of mRNA corresponding to SEQ ID NO:1 comprising a nucleotide as cited above, or where the antisense strand hybridizes under physiological conditions to a portion of mRNA corresponding to SEQ ID NO:2 beginning at nucleotide 124, 328, 387, 391, 393, 395, 406, 421, 423, 444, 447, 455, 459, 460, 467, 469, 470, 471, 475, 479, 513, 517, 531, 543, 556, 576, 587, 588, 589, 595, 601, 602, 611, 612, 651, 664, 667, 668, 669, 677, 678, 785, 786, 788, 791, 792, 804, 813, 824, 838, 843, 877, 884, 929, 959, 960, 961, 963, 964, 965, 970, 973, 974, 1000, 1002, 1013, 1026, 1053, 1056, 1057, 1058, 1161, 1315, 1318, 1324, 1357, 1360, 1383, 1393, 1420, 1471, 1573, 1671, 2044, 2045, 2046, 2047, 2048, 2089, 2090, 2091, 2092, or 2098.

When a first interfering RNA targets SEQ ID NO:1, the second interfering RNA may target either SEQ ID NO:1 or SEQ ID NO:2, and conversely, when a first interfering RNA targets SEQ ID NO:2, the second interfering RNA may target either SEQ ID NO:1 or SEQ ID NO:2. In further embodiments, a third, fourth, or more interfering RNAs may be administered.

A further embodiment of the invention is a method of treating a TNFα-related condition in a subject in need thereof, where the method comprises administering to the subject a composition comprising a double stranded siRNA molecule that down regulates expression of a TACE gene via RNA interference, wherein each strand of the siRNA molecule is independently about 19 to about 27 nucleotides in length; and one strand of the siRNA molecule comprises a nucleotide sequence having substantial complementarity to an mRNA corresponding to the TACE gene, so that the siRNA molecule directs cleavage of the mRNA via RNA interference.

A further embodiment of the invention is a method of treating a TNFα-related ocular condition in a subject in need thereof, where the method comprises administering to the subject a composition comprising a double stranded siRNA molecule that down regulates expression of a TNFR1 gene via RNA interference, wherein each strand of the siRNA molecule is independently about 19 to about 27 nucleotides in length; and one strand of the siRNA molecule comprises a nucleotide sequence having substantial complementarity to an mRNA corresponding to the TNFR1 gene so that the siRNA molecule directs cleavage of the mRNA via RNA interference.

A method of attenuating expression of TACE mRNA of the subject, comprising administering to the subject a composition comprising an effective amount of a single-stranded interfering RNA and a pharmaceutically acceptable carrier is a further embodiment. The single-stranded interfering RNA has a length of 19 to 49 nucleotides and hybridizes under physiological conditions to a portion of mRNA corresponding to SEQ ID NO:1 comprising nucleotide 297, 333, 334, 335, 434, 470, 493, 547, 570, 573, 618, 649, 689, 755, 842, 844, 846, 860, 878, 894, 900, 909, 910, 913, 942, 970, 984, 1002, 1010, 1053, 1064, 1137, 1162, 1215, 1330, 1334, 1340, 1386, 1393, 1428, 1505, 1508, 1541, 1553, 1557, 1591, 1592, 1593, 1597, 1604, 1605, 1626, 1632, 1658, 1661, 1691, 1794, 1856, 1945, 1946, 1947, 1958, 2022, 2094, 2100, 2121, 2263, 2277, 2347, 2349, 2549, 2578, 2595, 2606, 2608, 2629, 2639, 2764, 2766, 2767, 2769, 3027, 3028, 3261, 3264, 3284, 3313, 3317, 3332, or 3337, and the interfering RNA has a region of at least near-perfect contiguous complementarity with the hybridizing portion of mRNA corresponding to SEQ ID NO: 1. The expression of TACE mRNA is thereby attenuated.

The invention includes as a further embodiment a composition comprising an interfering RNA having a length of 19 to 49 nucleotides, and comprising a nucleotide sequence corresponding to any one of SEQ ID NO:3, SEQ ID NO:14-SEQ ID NO:58, and SEQ ID NO:155-SEQ ID NO:201, or a complement thereof; and a pharmaceutically acceptable carrier.

The invention includes as a further embodiment a composition comprising an interfering RNA consisting essentially of a nucleotide sequence corresponding to any one of SEQ ID NO:59-SEQ ID NO:69, SEQ ID NO:71-SEQ ID NO:92, and SEQ ID NO:94-SEQ ID NO:154, or a complement thereof; and a pharmaceutically acceptable carrier.

Use of any of the embodiments as described herein in the preparation of a medicament for attenuating expression of TACE mRNA or of TNFR1 mRNA as a method of attenuating activity of TNFα and thereby treating a TNFα-related condition as set forth herein is also an embodiment of the present invention.

BRIEF DESCRIPTION OF THE FIGURES

In order that the manner in which the above recited and other advantages and objects of the invention are obtained, a more particular description of the invention briefly described above will be rendered by reference to specific embodiments thereof, which are illustrated, in the appended drawings. Understanding that these drawings depict only typical embodiments of the invention and are therefore not to be considered limiting of its scope, the invention will be described with additional specificity and detail through the use of the accompanying drawings in which:

FIG. 1 provides a TNFR1 western blot of GTM-3 cells transfected with TNFR1 siRNAs #1, #2, #3, and #4, and a RISC-free control siRNA, each at 10 nM, 1 nM, and 0.1 nM; a non-targeting control siRNA (NTC2) at 10 nM; and a buffer control (-siRNA). The arrows indicate the positions of the 55-kDa TNFR1 and 42-kDa actin bands.

DETAILED DESCRIPTION OF THE INVENTION

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3$^{rd}$ Edition.

As used herein, all percentages are percentages by weight, unless stated otherwise.

As used herein and unless otherwise indicated, the terms "a" and "an" are taken to mean "one", "at least one" or "one or more".

The term "dry eye," also known as conjunctivitis sicca or keratoconjunctivitis sicca, is a common ophthalmological disorder involving breakdown of the pre-ocular tear film, resulting in dehydration of the exposed outer surface of the eye.

The term "ocular inflammation," as used herein, includes iritis, uveitis, episcleritis, scleritis, keratitis, endophthalmitis, blepharitis, and iatrogenic inflammatory conditions, for example.

The term "allergic conjunctivitis," as used herein, refers to inflammation of the conjunctiva which is the delicate membrane that lines the eyelids and covers the exposed surface of the sclera. The term "allergic conjunctivitis" includes, for example, atopic keratoconjunctivitis, giant papillary conjunctivitis, hay fever conjunctivitis, perennial allergic conjunctivitis, and vernal keratoconjunctivitis.

The term "dermatitis," as used herein, refers to inflammation of the skin and includes, for example, allergic contact dermatitis, urticaria, asteatotic dermatitis (dry skin on the lower legs), atopic dermatitis, contact dermatitis including irritant contact dermatitis and urushiol-induced contact dermatitis, eczema, gravitational dermatitis, nummular dermatitis, otitis externa, perioral dermatitis, and seborrhoeic dermatitis.

The term "rhinitis," as used herein, refers to inflammation of the mucous membranes of the nose and includes, for example, allergic rhinitis, atopic rhinitis, irritant rhinitis, eosinophilic non-allergic rhinitis, rhinitis medicamentosa, and neutrophilic rhinosinusitis.

The term "asthma," as used herein, refers to inflammation of the air passages resulting in narrowing of the airways that transport air from the nose and mouth to the lungs and includes, for example, allergic asthma, atopic asthma, atopic bronchial IgE-mediated asthma, bronchial asthma, bronchiolytis, emphysematous asthma, essential asthma, exercise-induced asthma, extrinsic asthma caused by environmental factors, incipient asthma, intrinsic asthma caused by pathophysiologic disturbances, non-allergic asthma, non-atopic asthma, and wheezy infant syndrome.

The phrase "a region of at least 13 contiguous nucleotides having at least 90% sequence complementarity to, or at least 90% sequence identity with, the penultimate 13 nucleotides of the 3' end of an mRNA corresponding to any one of (a sequence identifier)" allows a one nucleotide substitution. Two nucleotide substitutions (i.e., 11/13=85% identity/complementarity) are not included in such a phrase.

The term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

As used herein, the term "hybridization" means and refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning: A Laboratory Manual*, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature ($T_m$) of the hybrid where $T_m$ is determined for hybrids between 19 and 49 base pairs in length using the following calculation: $T_m° C.=81.5+16.6(\log_{10}[Na+])+0.41$ (% G+C)−(600/N) where N is the number of bases in the hybrid, and [Na+] is the concentration of sodium ions in the hybridization buffer.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

An mRNA sequence is readily deduced from the sequence of the corresponding DNA sequence. For example, SEQ ID NO:1 provides the sense strand sequence of DNA corresponding to the mRNA for TACE. The mRNA sequence is identical to the DNA sense strand sequence with the "T" bases replaced with "U" bases. Therefore, the mRNA sequence of TACE is known from SEQ ID NO:1 and the mRNA of TNFR1 is known from SEQ ID NO:2.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA. Other RNA molecules and RNA-like molecules can also interact with RISC and silence gene expression. Examples of other RNA molecules that can interact with RISC include short hairpin RNAs (shRNAs), single-stranded siRNAs, microRNAs (miRNAs), and dicer-substrate 27-mer duplexes. The term "siRNA" as used herein refers to a double-stranded interfering RNA unless otherwise noted. Examples of RNA-like molecules that can interact with RISC include RNA molecules containing one or more chemically modified nucleotides, one or more deoxyribonucleotides, and/or one or more non-phosphodiester linkages. For purposes of the present discussion, all RNA or RNA-like molecules that can interact with RISC and participate in RISC-mediated changes in gene expression will be referred to as "interfering RNAs." SiRNAs, shRNAs, miRNAs, and dicer-substrate 27-mer duplexes are, therefore, subsets of "interfering RNAs."

Interfering RNA of embodiments of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

The present invention relates to the use of interfering RNA to inhibit the expression of TNFα cell surface receptor TNF receptor-1 (TNFR1), or the TNFα converting enzyme (TACE/ADAM17, designated herein "TACE") which inhibition effects reduction of tumor necrosis factor α (TNFα) activity. Binding of TNFα to its cell surface receptor, TNF receptor-1 (TNFR1), activates a signaling cascade which affects a variety of cellular responses including apoptosis and inflammation. TNFα itself is initially expressed as an inactive, membrane-bound precursor. Release of the active form of TNFα from the cell surface requires proteolytic processing of the precursor by TNFα converting enzyme (TACE/ADAM17), a member of the 'A Disintegrin And Metalloprotease' (ADAM) family.

According to the present invention, inhibiting the expression of TNFR1 mRNA, TACE mRNA, or both TNFR1 and TACE mRNAs effectively reduces the action of TNFα. Further, interfering RNAs as set forth herein provided exogenously or expressed endogenously are particularly effective at silencing TNFR1 mRNA or TACE mRNA.

Tumor Necrosis Factor α Converting Enzyme mRNA (TACE/ADAM17):

The GenBank database provides the DNA sequence for TACE as accession no. NM_003183, provided in the "Sequence Listing" as SEQ ID NO:1. SEQ ID NO:1 provides the sense strand sequence of DNA that corresponds to the mRNA encoding TACE (with the exception of "T" bases for "U" bases). The coding sequence for TACE is from nucleotides 184-2658.

Equivalents of the above cited TACE mRNA sequence are alternative splice forms, allelic forms, isozymes, or a cognate thereof. A cognate is a tumor necrosis factor α converting enzyme mRNA from another mammalian species that is homologous to SEQ ID NO:1 (i.e., an ortholog).

Tumor Necrosis Factor Receptor-1 mRNA (TNFR1):

The GenBank database provides the DNA sequence for TNFR1 as accession no. NM_001065, provided in the "Sequence Listing" as SEQ ID NO:2. SEQ ID NO:2 provides the sense strand sequence of DNA that corresponds to the mRNA encoding TNFR1 (with the exception of "T" bases for "U" bases). The coding sequence for TNFR1 is from nucleotides 282-1649.

Equivalents of the above cited TNFR1 mRNA sequence are alternative splice forms, allelic forms, isozymes, or a cognate thereof. A cognate is a tumor necrosis factor receptor-1 mRNA from another mammalian species that is homologous to SEQ ID NO:2 (i.e., an ortholog).

Attenuating Expression of an mRNA:

The phrase, "attenuating expression of an mRNA," as used herein, means administering or expressing an amount of interfering RNA (e.g., an siRNA) to reduce translation of the target mRNA into protein, either through mRNA cleavage or through direct inhibition of translation. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention. In one embodiment, a single interfering RNA targeting TACE mRNA or TNFR1 mRNA is administered. In other embodiments, two or more interfering RNAs targeting TACE mRNA or TNFR1 mRNA are administered. In further embodiments, interfering RNAs targeting each of TACE mRNA and TNFR1 mRNA are administered in combination or in a time interval so as to have overlapping effects.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Inhibition of TACE or TNFR1 may also be determined in vitro by evaluating target mRNA levels or target protein levels in, for example, human corneal epithelial cells following transfection of TACE- or TNFR1-interfering RNA as described infra.

Inhibition of TNFα activity due to inhibition of TACE mRNA expression or of TNFR1 mRNA expression is also inferred in a human or mammal by observing an improvement in a TNFα-related condition symptom such as improvement in symptoms related to dry eye, allergic conjunctivitis, ocular inflammation, dermatitis, rhinitis, or asthma. Improvement in any of dry eye symptoms, edema, itching, inflammation, or tolerance to environmental challenges, for example, is indicative of inhibition of TNFα activity.

Interfering RNA:

In one embodiment of the invention, interfering RNA (e.g., siRNA) has a sense strand and an antisense strand, and the sense and antisense strands comprise a region of at least near-perfect contiguous complementarity of at least 19 nucleotides. In a further embodiment of the invention, interfering RNA (e.g., siRNA) has a sense strand and an antisense strand, and the antisense strand comprises a region of at least near-perfect contiguous complementarity of at least 19 nucleotides to a target sequence of TACE mRNA or TNFR1 mRNA, and the sense strand comprises a region of at least near-perfect contiguous identity of at least 19 nucleotides with a target sequence of TACE mRNA or TNFR1 mRNA, respectively. In a further embodiment of the invention, the interfering RNA comprises a region of at least 13, 14, 15, 16, 17, or 18 contiguous nucleotides having percentages of sequence complementarity to or, having percentages of sequence identity with, the penultimate 13, 14, 15, 16, 17, or 18 nucleotides, respectively, of the 3' end of the corresponding target sequence within an mRNA.

The length of each strand of the interfering RNA comprises 19 to 49 nucleotides, and may comprise a length of 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression.

In embodiments of the present invention, interfering RNA target sequences (e.g., siRNA target sequences) within a target mRNA sequence are selected using available design tools. Interfering RNAs corresponding to a TACE or TNFR1 target sequence are then tested by transfection of cells expressing the target mRNA followed by assessment of knockdown as described above.

Techniques for selecting target sequences for siRNAs are provided by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNAs.

An embodiment of a 19-nucleotide DNA target sequence for TACE mRNA is present at nucleotides 297 to 315 of SEQ ID NO:1:

```
5'- GCTCTCAGACTACGATATT -3'    SEQ ID NO: 3.
```

An siRNA of the invention for targeting a corresponding mRNA sequence of SEQ ID NO:3 and having 21-nucleotide strands and a 2-nucleotide 3' overhang is:

```
5'- GCUCUCAGACUACGAUAUUNN -3'    SEQ ID NO: 4

3'- NNCGAGAGUCUGAUGCUAUAA -5'    SEQ ID NO: 5.
```

Each "N" residue can be any nucleotide (A, C, G, U, T) or modified nucleotide. The 3' end can have a number of "N" residues between and including 1, 2, 3, 4, 5, and 6. The "N" residues on either strand can be the same residue (e.g., UU, AA, CC, GG, or TT) or they can be different (e.g., AC, AG, AU, CA, CG, CU, GA, GC, GU, UA, UC, or UG). The 3' overhangs can be the same or they can be different. In one embodiment, both strands have a 3'UU overhang.

An siRNA of the invention for targeting a corresponding mRNA sequence of SEQ ID NO:3 and having 21-nucleotide strands and a 3'UU overhang on each strand is:

```
5'- GCUCUCAGACUACGAUAUUUU -3'    SEQ ID NO: 6

3'- UUCGAGAGUCUGAUGCUAUAA -5'    SEQ ID NO: 7.
```

The interfering RNA may also have a 5' overhang of nucleotides or it may have blunt ends. An siRNA of the invention for targeting a corresponding mRNA sequence of SEQ ID NO:3 and having 19-nucleotide strands and blunt ends is:

```
5'- GCUCUCAGACUACGAUAUU -3'    SEQ ID NO: 8

3'- CGAGAGUCUGAUGCUAUAA -5'    SEQ ID NO: 9.
```

The strands of a double-stranded interfering RNA (e.g., an siRNA) may be connected to form a hairpin or stem-loop structure (e.g., an shRNA). An shRNA of the invention targeting a corresponding mRNA sequence of SEQ ID NO:3 and having a 19 bp double-stranded stem region and a 3'UU overhang is:

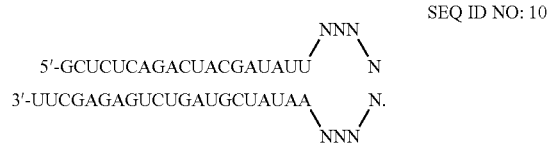

SEQ ID NO: 10

N is a nucleotide A, T, C, G, U, or a modified form known by one of ordinary skill in the art. The number of nucleotides N in the loop is a number between and including 3 to 23, or 5 to 15, or 7 to 13, or 4 to 9, or 9 to 11, or the number of nucleotides N is 9. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) *Science* 296: 550) and 5'-UUUGUGUAG-3' (Castanotto, D. et al. (2002) *RNA* 8:1454). It will be recognized by one of skill in the art that the resulting single chain oligonucleotide forms a stem-loop or hairpin structure comprising a double-stranded region capable of interacting with the RNAi machinery.

The siRNA target sequence identified above can be extended at the 3' end to facilitate the design of dicer-substrate 27-mer duplexes. Extension of the 19-nucleotide DNA target sequence (SEQ ID NO:3) identified in the TACE DNA sequence (SEQ ID NO:1) by 6 nucleotides yields a 25-nucleotide DNA target sequence present at nucleotides 297 to 321 of SEQ ID NO:1:

```
5'- GCTCTCAGACTACGATATTCTCTCT -3'  SEQ ID NO: 11.
```

A dicer-substrate 27-mer duplex of the invention for targeting a corresponding mRNA sequence of SEQ ID NO:11 is:

```
5'-  GCUCUCAGACUACGAUAUUCUCUCU -3'  SEQ ID NO: 12

3'- UUCGAGAGUCUGAUGCUAUAAGAGAGA -5'  SEQ ID NO: 13.
```

The two nucleotides at the 3' end of the sense strand (i.e., the CU nucleotides of SEQ ID NO:12) may be deoxynucleotides for enhanced processing. Design of dicer-substrate 27-mer duplexes from 19-21 nucleotide target sequences, such as provided herein, is further discussed by the Integrated DNA Technologies (IDT) website and by Kim, D.-H. et al., (February, 2005) *Nature Biotechnology* 23:2; 222-226.

When interfering RNAs are produced by chemical synthesis, phosphorylation at the 5' position of the nucleotide at the 5' end of one or both strands (when present) can enhance siRNA efficacy and specificity of the bound RISC complex but is not required since phosphorylation can occur intracellularly.

Table 1 lists examples of TACE DNA target sequences of SEQ ID NO:1 from which siRNAs of the present invention are designed in a manner as set forth above. TACE encodes tumor necrosis factor α converting enzyme, as noted above.

TABLE 1

TACE Target Sequences for siRNAs

| TACE Target Sequence | # of Starting Nucleotide with reference to SEQ ID NO: 1 | SEQ ID NO: |
|---|---|---|
| GCTCTCAGACTACGATATT | 297 | 3 |
| CCAGCAGCATTCGGTAAGA | 333 | 14 |
| CAGCAGCATTCGGTAAGAA | 334 | 15 |
| AGCAGCATTCGGTAAGAAA | 335 | 16 |
| AGAGATCTACAGACTTCAA | 355 | 17 |
| GAAAGCGAGTACACTGTAA | 493 | 18 |
| CCATGAAGAACACGTGTAA | 842 | 19 |
| GAAGAACACGTGTAAATTA | 846 | 20 |
| ATCATCGCTTCTACAGATA | 878 | 21 |
| AGAGCAATTTAGCTTTGAT | 1137 | 22 |
| GGTTTGACGAGCACAAAGA | 1330 | 23 |
| TGATCCGGATGGTCTAGCA | 1428 | 24 |
| GCGATCACGAGAACAATAA | 1508 | 25 |
| GCAGTAAACAATCAATCTA | 1541 | 26 |
| CAATCTATAAGACCATTGA | 1553 | 27 |
| TTTCAAGAACGCAGCAATA | 1591 | 28 |
| TTCAAGAACGCAGCAATAA | 1592 | 29 |

TABLE 1-continued

TACE Target Sequences for siRNAs

| TACE Target Sequence | # of Starting Nucleotide with reference to SEQ ID NO: 1 | SEQ ID NO: |
|---|---|---|
| TCAAGAACGCAGCAATAAA | 1593 | 30 |
| TCATGTATCTGAACAACGA | 1661 | 31 |
| ACAGCGACTGCACGTTGAA | 1691 | 32 |
| GATTAATGCTACTTGCAAA | 1794 | 33 |
| CTGGAGTCCTGTGCATGTA | 1945 | 34 |
| TGGAGTCCTGTGCATGTAA | 1946 | 35 |
| GGAGTCCTGTGCATGTAAT | 1947 | 36 |
| CATGTAATGAAACTGACAA | 1958 | 37 |
| CTATGTCGATGCTGAACAA | 2022 | 38 |
| CAAATGTGAGAAACGAGTA | 2100 | 39 |
| GCATCGGTTCGCATTATCA | 2347 | 40 |
| ATCGGTTCGCATTATCAAA | 2349 | 41 |
| CCAAGTCATTTGAGGATCT | 2549 | 42 |
| CCGGTCACCAGAAGTGAAA | 2578 | 43 |
| AAAGGCTGCCTCCTTTAAA | 2595 | 44 |
| TTTAAACTGCAGCGTCAGA | 2608 | 45 |
| AGATGCTGGTCATGTGTTT | 2764 | 46 |
| ATGCTGGTCATGTGTTTGA | 2766 | 47 |
| TGCTGGTCATGTGTTTGAA | 2767 | 48 |
| CTGGTCATGTGTTTGAACT | 2769 | 49 |
| TGTAATGAACCGCTGAATA | 3027 | 50 |
| GTAATGAACCGCTGAATAT | 3028 | 51 |
| CTAAGACTAATGCTCTCTA | 3261 | 52 |
| AGACTAATGCTCTCTAGAA | 3264 | 53 |
| CCTAACCACCTACCTTACA | 3284 | 54 |
| TACATGGTAGCCAGTTGAA | 3313 | 55 |
| TGGTAGCCAGTTGAATTTA | 3317 | 56 |
| TTTATGGAATCTACCAACT | 3332 | 57 |
| GGAATCTACCAACTGTTTA | 3337 | 58 |
| CATCAAGTACTGAACGTTT | 434 | 155 |
| TCGTGGTGGTGGATGGTAA | 470 | 156 |
| GAAAGCGAGTACACTGTAA | 493 | 157 |
| GAGCCTGACTCTAGGGTTC | 547 | 158 |
| CCACATAAGAGATGATGAT | 570 | 159 |
| CATAAGAGATGATGATGTT | 573 | 160 |
| CGAATATAACATAGAGCCA | 618 | 161 |
| GTTAATGATACCAAAGACA | 649 | 162 |
| CTGAAGATATCAAGAATGT | 689 | 163 |
| ATGAAGAGTTGCTCCCAAA | 755 | 164 |
| ATGAAGAACACGTGTAAAT | 844 | 165 |
| AATTATTGGTGGTAGCAGA | 860 | 166 |
| ATCATCGCTTCTACAGATA | 878 | 167 |
| ATACATGGGCAGAGGGGAA | 894 | 168 |
| GGGCAGAGGGGAAGAGAGT | 900 | 169 |
| GGAAGAGAGTACAACTACA | 909 | 170 |
| GAAGAGAGTACAACTACAA | 910 | 171 |
| GAGAGTACAACTACAAATT | 913 | 172 |
| GCTAATTGACAGAGTTGAT | 942 | 173 |
| CGGAACACTTCATGGGATA | 970 | 174 |
| GGATAATGCAGGTTTTAAA | 984 | 175 |
| AGGCTATGGAATACAGATA | 1002 | 176 |
| GAATACAGATAGAGCAGAT | 1010 | 177 |
| GGTAAAACCTGGTGAAAAG | 1053 | 178 |
| GTGAAAAGCACTACAACAT | 1064 | 179 |
| GAGGAAGCATCTAAAGTTT | 1162 | 180 |
| TATGGGAACTCTTGGATTA | 1215 | 181 |
| TGACGAGCACAAAGAATTA | 1334 | 182 |
| GCACAAAGAATTATGGTAA | 1340 | 183 |
| GGTTACAACTCATGAATTG | 1386 | 184 |
| ACTCATGAATTGGGACATA | 1393 | 185 |
| GTGGCGATCACGAGAACAA | 1505 | 186 |
| CTATAAGACCATTGAAAGT | 1557 | 187 |
| GAACGCAGCAATAAAGTTT | 1597 | 188 |
| GCAATAAAGTTTGTGGGAA | 1604 | 189 |
| CAATAAAGTTTGTGGGAAC | 1605 | 190 |
| GAGGGTGGATGAAGGAGAA | 1626 | 191 |
| GGATGAAGGAGAAGAGTGT | 1632 | 192 |
| GCATCATGTATCTGAACAA | 1658 | 193 |
| CAGGAAATGCTGAAGATGA | 1856 | 194 |
| GAATGGCAAATGTGAGAAA | 2094 | 195 |
| GGATGTAATTGAACGATTT | 2121 | 196 |
| GTGGATAAGAAATTGGATA | 2263 | 197 |
| GGATAAACAGTATGAATCT | 2277 | 198 |

TABLE 1-continued

TACE Target Sequences for siRNAs

| TACE Target Sequence | # of Starting Nucleotide with reference to SEQ ID NO: 1 | SEQ ID NO: |
|---|---|---|
| CCTTTAAACTGCAGCGTCA | 2606 | 199 |
| CGTGTTGACAGCAAAGAAA | 2629 | 200 |
| GCAAAGAAACAGAGTGCTA | 2639 | 201 |

Table 2 lists examples of TNFR1 DNA target sequences of SEQ ID NO:2 from which siRNAs of the present invention are designed in a manner as set forth above. TNFR1 encodes tumor necrosis factor α receptor-1, as noted above.

TABLE 2

TNFR1 Target Sequences for siRNAs

| TNFR1 Target Sequence | # of Starting Nucleotide with reference to SEQ ID NO: 2 | SEQ ID NO: |
|---|---|---|
| ACCAGGCCGTGATCTCTAT | 124 | 59 |
| AATTCGATTTGCTGTACCA | 444 | 60 |
| TCGATTTGCTGTACCAAGT | 447 | 61 |
| ACAAAGGAACCTACTTGTA | 469 | 62 |
| GAACCTACTTGTACAATGA | 475 | 63 |
| CTACTTGTACAATGACTGT | 479 | 64 |
| TGTGAGAGCGGCTCCTTCA | 531 | 65 |
| TCAGGTGGAGATCTCTTCT | 611 | 66 |
| CAGGTGGAGATCTCTTCTT | 612 | 67 |
| AGAACCAGTACCGGCATTA | 667 | 68 |
| GAACCAGTACCGGCATTAT | 668 | 69 |
| AACCAGTACCGGCATTATT | 669 | 70 |
| CCGGCATTATTGGAGTGAA | 677 | 71 |
| CGGCATTATTGGAGTGAAA | 678 | 72 |
| AGCCTGGAGTGCACGAAGT | 843 | 73 |
| CTCCTCTTCATTGGTTTAA | 960 | 74 |
| TTGGTTTAATGTATCGCTA | 970 | 75 |
| GTTTAATGTATCGCTACCA | 973 | 76 |
| TTTAATGTATCGCTACCAA | 974 | 77 |
| AGTCCAAGCTCTACTCCAT | 1000 | 78 |
| GAGCTTGAAGGAACTACTA | 1053 | 79 |
| CTTGAAGGAACTACTACTA | 1056 | 80 |
| TTGAAGGAACTACTACTAA | 1057 | 81 |
| ACAAGCCACAGAGCCTAGA | 1318 | 82 |
| TGTACGCCGTGGTGGAGAA | 1357 | 83 |

TABLE 2 -continued

TNFR1 Target Sequences for siRNAs

| TNFR1 Target Sequence | # of Starting Nucleotide with reference to SEQ ID NO: 2 | SEQ ID NO: |
|---|---|---|
| CCGTTGCGCTGGAAGGAAT | 1383 | 84 |
| TCTAAGGACCGTCCTGCGA | 1671 | 85 |
| CTAATAGAAACTTGGCACT | 2044 | 86 |
| TAATAGAAACTTGGCACTC | 2045 | 87 |
| AATAGAAACTTGGCACTCC | 2046 | 88 |
| ATAGAAACTTGGCACTCCT | 2047 | 89 |
| TAGAAACTTGGCACTCCTG | 2048 | 90 |
| ATAGCAAGCTGAACTGTCC | 2089 | 91 |
| TAGCAAGCTGAACTGTCCT | 2090 | 92 |
| AGCAAGCTGAACTGTCCTA | 2091 | 93 |
| GCAAGCTGAACTGTCCTAA | 2092 | 94 |
| TGAACTGTCCTAAGGCAGG | 2098 | 95 |
| CAAAGGAACCTACTTGTAC | 470 | 96 |
| GAGCTTGAAGGAACTACTA | 1053 | 97 |
| CACAGAGCCTAGACACTGA | 1324 | 98 |
| TCCAAGCTCTACTCCATTG | 1002 | 99 |
| TGGAGCTGTTGGTGGGAAT | 328 | 100 |
| GACAGGGAGAAGAGAGATA | 387 | 101 |
| GGGAGAAGAGAGATAGTGT | 391 | 102 |
| GAGAAGAGAGATAGTGTGT | 393 | 103 |
| GAAGAGAGATAGTGTGTGT | 395 | 104 |
| GTGTGTGTCCCCAAGGAAA | 406 | 105 |
| GAAAATATATCCACCCTCA | 421 | 106 |
| AAATATATCCACCCTCAAA | 423 | 107 |
| CTGTACCAAGTGCCACAAA | 455 | 108 |
| ACCAAGTGCCACAAAGGAA | 459 | 109 |
| CCAAGTGCCACAAAGGAAC | 460 | 110 |
| CCACAAAGGAACCTACTTG | 467 | 111 |
| CAAAGGAACCTACTTGTAC | 470 | 112 |
| AAAGGAACCTACTTGTACA | 471 | 113 |
| GATACGGACTGCAGGGAGT | 513 | 114 |
| CGGACTGCAGGGAGTGTGA | 517 | 115 |
| TCCTTCACCGCTTCAGAAA | 543 | 116 |
| CAGAAACCACCTCAGACA | 556 | 117 |
| TGCCTCAGCTGCTCCAAAT | 576 | 118 |
| CTCCAAATGCCGAAAGGAA | 587 | 119 |
| TCCAAATGCCGAAAGGAAA | 588 | 120 |

TABLE 2 -continued

TNFR1 Target Sequences for siRNAs

| TNFR1 Target Sequence | # of Starting Nucleotide with reference to SEQ ID NO: 2 | SEQ ID NO: |
|---|---|---|
| CCAAATGCCGAAAGGAAAT | 589 | 121 |
| GCCGAAAGGAAATGGGTCA | 595 | 122 |
| AGGAAATGGGTCAGGTGGA | 601 | 123 |
| GGAAATGGGTCAGGTGGAG | 602 | 124 |
| GTGTGTGGCTGCAGGAAGA | 651 | 125 |
| GGAAGAACCAGTACCGGCA | 664 | 126 |
| CCATGCAGGTTTCTTTCTA | 785 | 127 |
| CATGCAGGTTTCTTTCTAA | 786 | 128 |
| TGCAGGTTTCTTTCTAAGA | 788 | 129 |
| AGGTTTCTTTCTAAGAGAA | 791 | 130 |
| GGTTTCTTTCTAAGAGAAA | 792 | 131 |
| AGAGAAAACGAGTGTGTCT | 804 | 132 |
| GAGTGTGTCTCCTGTAGTA | 813 | 133 |
| CTGTAGTAACTGTAAGAAA | 824 | 134 |
| AGAAAAGCCTGGAGTGCAC | 838 | 135 |
| TTGAGAATGTTAAGGGCAC | 877 | 136 |
| TGTTAAGGGCACTGAGGAC | 884 | 137 |
| GGTCATTTTCTTTGGTCTT | 929 | 138 |
| CCTCCTCTTCATTGGTTTA | 959 | 139 |
| TCCTCTTCATTGGTTTAAT | 961 | 140 |
| CTCTTCATTGGTTTAATGT | 963 | 141 |
| TCTTCATTGGTTTAATGTA | 964 | 142 |
| CTTCATTGGTTTAATGTAT | 965 | 143 |
| TCCAAGCTCTACTCCATTG | 1002 | 144 |
| CTCCATTGTTTGTGGGAAA | 1013 | 145 |
| GGGAAATCGACACCTGAAA | 1026 | 146 |
| TGAAGGAACTACTACTAAG | 1058 | 147 |
| ACCTCCAGCTCCACCTATA | 1161 | 148 |
| CCCACAAGCCACAGAGCCT | 1315 | 149 |
| ACGCCGTGGTGGAGAACGT | 1360 | 150 |
| GGAAGGAATTCGTGCGGCG | 1393 | 151 |
| TGAGCGACCACGAGATCGA | 1420 | 152 |
| GCGAGGCGCAATACAGCAT | 1471 | 153 |
| TGGGCTGCCTGGAGGACAT | 1573 | 154 |

As cited in the examples above, one of skill in the art is able to use the target sequence information provided in Tables 1 or 2 to design interfering RNAs having a length shorter or longer than the sequences provided in the tables and by referring to the sequence position in SEQ ID NO:1 or SEQ ID NO:2 and adding or deleting nucleotides complementary or near complementary to SEQ ID NO:1 or SEQ ID NO:2, respectively.

The target RNA cleavage reaction guided by siRNAs and other forms of interfering RNA is highly sequence specific. In general, siRNA containing a sense nucleotide strand identical in sequence to a portion of the target mRNA and an antisense nucleotide strand exactly complementary to a portion of the target mRNA are siRNA embodiments for inhibition of mRNAs cited herein. However, 100% sequence complementarity between the antisense siRNA strand and the target mRNA, or between the antisense siRNA strand and the sense siRNA strand, is not required to practice the present invention. Thus, for example, the invention allows for sequence variations that might be expected due to genetic mutation, strain polymorphism, or evolutionary divergence.

In one embodiment of the invention, the antisense strand of the siRNA has at least near-perfect contiguous complementarity of at least 19 nucleotides with the target mRNA. "Near-perfect," as used herein, means the antisense strand of the siRNA is "substantially complementary to," and the sense strand of the siRNA is "substantially identical" to at least a portion of the target mRNA. "Identity," as known by one of ordinary skill in the art, is the degree of sequence relatedness between nucleotide sequences as determined by matching the order and identity of nucleotides between the sequences. In one embodiment, the antisense strand of an siRNA having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) *J. Mol. Biol.* 215:403-410).

The relationship between a target mRNA (sense strand) and one strand of an siRNA (the sense strand) is that of identity. The sense strand of an siRNA is also called a passenger strand, if present. The relationship between a target mRNA (sense strand) and the other strand of an siRNA (the antisense strand) is that of complementarity. The antisense strand of an siRNA is also called a guide strand.

The penultimate base in a nucleic acid sequence that is written in a 5' to 3' direction is the next to the last base, i.e., the base next to the 3' base. The penultimate 13 bases of a nucleic acid sequence written in a 5' to 3' direction are the last 13 bases of a sequence next to the 3' base and not including the 3' base. Similarly, the penultimate 14, 15, 16, 17, or 18 bases of a nucleic acid sequence written in a 5' to 3' direction are the last 14, 15, 16, 17, or 18 bases of a sequence, respectively, next to the 3' base and not including the 3' base.

In an embodiment of the invention, the region of contiguous nucleotides is a region of at least 13 contiguous nucleotides having at least 90% sequence complementarity to, or at least 90% sequence identity with, the penultimate 13 nucleotides of the 3' end of an mRNA corresponding to the sequence identified by each sequence identifier.

In one embodiment of the invention, the region of contiguous nucleotides is a region of at least 14 contiguous nucleotides having at least 85% sequence complementarity to, or at least 85% sequence identity with, the penultimate 14 nucleotides of the 3' end of an mRNA corresponding to the sequence identified by each sequence identifier. Two nucleotide substitutions (i.e., 12/14=86% identity/complementarity) are included in such a phrase.

In a further embodiment of the invention, the region of contiguous nucleotides is a region of at least 15, 16, 17, or 18 contiguous nucleotides having at least 80% sequence complementarity to, or at least 80% sequence identity with, the penultimate 14 nucleotides of the 3' end of an mRNA corresponding to the sequence of the sequence identifier. Three nucleotide substitutions are included in such a phrase.

The target sequence in the mRNAs corresponding to SEQ ID NO:1 or SEQ ID NO:2 may be in the 5' or 3' untranslated regions of the mRNA as well as in the coding region of the mRNA.

One or both of the strands of double-stranded interfering RNA may have a 3' overhang of from 1 to 6 nucleotides, which may be ribonucleotides or deoxyribonucleotides or a mixture thereof. The nucleotides of the overhang are not base-paired. In one embodiment of the invention, the interfering RNA comprises a 3' overhang of TT or UU. In another embodiment of the invention, the interfering RNA comprises at least one blunt end. The termini usually have a 5' phosphate group or a 3' hydroxyl group. In other embodiments, the antisense strand has a 5' phosphate group, and the sense strand has a 5' hydroxyl group. In still other embodiments, the termini are further modified by covalent addition of other molecules or functional groups.

The sense and antisense strands of the double-stranded siRNA may be in a duplex formation of two single strands as described above or may be a single molecule where the regions of complementarity are base-paired and are covalently linked by a hairpin loop so as to form a single strand. It is believed that the hairpin is cleaved intracellularly by a protein termed dicer to form an interfering RNA of two individual base-paired RNA molecules.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

There may be a region or regions of the antisense interfering RNA strand that is (are) not complementary to a portion of SEQ ID NO:1 or SEQ ID NO:2. Non-complementary regions may be at the 3', 5' or both ends of a complementary region or between two complementary regions.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNAs can also be expressed endogenously from plasmid or viral expression vectors or from minimal expression cassettes, for example, PCR generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Mirus, Madison, Wis.). A first interfering RNA may be administered via in vivo expression from a first expression vector capable of expressing the first interfering RNA and a second interfering RNA may be administered via in vivo expression from a second expression vector capable of expressing the second interfering RNA, or both interfering RNAs may be administered via in vivo expression from a single expression vector capable of expressing both interfering RNAs.

Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

Hybridization under Physiological Conditions:

In certain embodiments of the present invention, an antisense strand of an interfering RNA hybridizes with an mRNA in vivo as part of the RISC complex.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning: A Laboratory Manual*, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature ($T_m$) of the hybrid where $T_m$ is determined for hybrids between 19 and 49 base pairs in length using the following calculation: $T_m°$ C.=$81.5+16.6(\log_{10}[Na+])+0.41$ (% G+C)−(600/N) where N is the number of bases in the hybrid, and [Na+] is the concentration of sodium ions in the hybridization buffer.

The above-described in vitro hybridization assay provides a method of predicting whether binding between a candidate siRNA and a target will have specificity. However, in the context of the RISC complex, specific cleavage of a target can also occur with an antisense strand that does not demonstrate high stringency for hybridization in vitro.

Single-Stranded Interfering RNA:

As cited above, interfering RNAs ultimately function as single strands. Single-stranded (ss) interfering RNA has been found to effect mRNA silencing, albeit less efficiently than double-stranded RNA. Therefore, embodiments of the present invention also provide for administration of a ss interfering RNA that hybridizes under physiological conditions to a portion of SEQ ID NO:1 or SEQ ID NO:2 and has a region of at least near-perfect contiguous complementarity of at least 19 nucleotides with the hybridizing portion of SEQ ID NO:1 or SEQ ID NO:2, respectively. The ss interfering RNA of Table 1 or Table 2 has a length of 19 to 49 nucleotides as for the ds interfering RNA cited above. The ss interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

SS interfering RNAs are synthesized chemically or by in vitro transcription or expressed endogenously from vectors or expression cassettes as for ds interfering RNAs. 5' Phosphate groups may be added via a kinase, or a 5' phosphate may be the result of nuclease cleavage of an RNA. Delivery is as for ds interfering RNAs. In one embodiment, ss interfering RNAs having protected ends and nuclease resistant modifications are administered for silencing. SS interfering RNAs may be dried for storage or dissolved in an aqueous solution. The solution may contain buffers or salts to inhibit annealing or for stabilization.

Hairpin Interfering RNA:

A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Mode of Administration:

Interfering RNA may be delivered via aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal administration, for example.

Administration may be directly to the eye by ocular tissue administration such as periocular, conjunctival, subtenon, intracameral, intravitreal, intraocular, subretinal, subconjunctival, retrobulbar, intracanalicular, or suprachoroidal administration; by injection, by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

Administration may be directly to the ear via, for example, topical otic drops or ointments, slow release devices in the ear or implanted adjacent to the ear. Local administration includes otic intramuscular, intratympanic cavity and intracochlear injection routes of administration. Furthermore, agents can be administered to the inner ear by placement of a gelfoam, or similar absorbent and adherent product, soaked with the interfering RNA against the window membrane of the middle/inner ear or adjacent structure.

Administration may be directly to the lungs, via, for example, an aerosolized preparation, and by inhalation via an inhaler or a nebulizer, for example.

Further modes of administration include tablets, pills, and capsules, all of which are capable of formulation by one of ordinary skill in the art.

Subject:

A subject in need of treatment for a TNFα-related condition or at risk for developing a TNFα-related condition is a human or other mammal having a TNFα-related inflammatory condition or having dry eye or at risk of developing a TNFα-related inflammatory condition or dry eye. A TNFα-related inflammatory condition includes, for example, allergic conjunctivitis, ocular inflammation, dermatitis, rhinitis, or asthma associated with undesired or inappropriate activity of TNFα as cited herein.

Ocular structures associated with a TNFα-related condition may include the eye, retina, choroid, lens, cornea, trabecular meshwork, iris, optic nerve, optic nerve head, sclera, aqueous chamber, vitreous chamber, ciliary body, or posterior segment, for example.

Otic structures associated with such disorders may include the inner ear, middle ear, outer ear, tympanic cavity or membrane, cochlea, or Eustachian tube, for example.

Pulmonary structures associated with such disorders may include the nose, mouth, pharynx, larynx, bronchial tubes, trachea, carina (the ridge separating the opening of the right and left main bronchi), and lungs, particularly the lower lungs, such as bronchioli and alveoli.

A subject may also be an otic cell, a lung cell, an ocular cell, cell culture, organ or an ex vivo organ or tissue.

Formulations and Dosage:

Pharmaceutical formulations comprise interfering RNAs, or salts thereof, of the invention up to 99% by weight mixed with a physiologically acceptable carrier medium such as water, buffer, saline, glycine, hyaluronic acid, mannitol, and the like.

Interfering RNAs of the present invention are administered as solutions, suspensions, or emulsions. The following are examples of possible formulations embodied by this invention.

|  | Amount in weight % |
|---|---|
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | Qs pH 7.4 |
| Purified water (RNase-free) | Qs 100 Ml |

|  | Amount in weight % |
|---|---|
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

|  | Amount in weight % |
|---|---|
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water (RNase-free) | q.s. to 100% |

|  | Amount in weight % |
|---|---|
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

Generally, an effective amount of the interfering RNAs of embodiments of the invention results in an extracellular concentration at the surface of the target cell of from 100 pM to 100 nM, or from 1 nM to 50 nM, or from 5 nM to about 10 nM, or about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions are delivered to the surface of the target organ one to four times per day, or on an extended delivery schedule such as daily, weekly, bi-weekly, monthly, or longer, according to the routine discretion of a skilled clinician. The pH of the formulation is about pH 4-9, or pH 4.5 to pH 7.4.

Therapeutic treatment of patients with siRNAs directed against TACE mRNA or TNFR1 mRNA is expected to be beneficial over small molecule treatments by increasing the duration of action, thereby allowing less frequent dosing and greater patient compliance.

An effective amount of a formulation may depend on factors such as the age, race, and sex of the subject, the severity of the TNFα-related condition, the rate of target gene transcript/protein turnover, the interfering RNA potency, and the interfering RNA stability, for example. In one embodiment, the interfering RNA is delivered topically to a target organ and reaches TACE mRNA- or TNFR1 mRNA-containing tissue at a therapeutic dose thereby ameliorating a TNFα-related process.

Acceptable Carriers:

An acceptable carrier refers to those carriers that cause at most, little to no ocular irritation, provide suitable preservation if needed, and deliver one or more interfering RNAs of the present invention in a homogenous dosage. An acceptable carrier for administration of interfering RNA of embodiments of the present invention include the cationic lipid-based transfection reagents TransIT®-TKO (Minis Corporation, Madison, Wis.), LIPOFECTIN®, Lipofectamine, OLIGOFECTAMINE™ (Invitrogen, Carlsbad, Calif.), or DHARMAFECT™ (Dharmacon, Lafayette, Colo.); polycations such as polyethyleneimine; cationic peptides such as Tat, polyarginine, or Penetratin (Antp peptide); or liposomes. Liposomes are formed from standard vesicle-forming lipids and a sterol, such as cholesterol, and may include a targeting molecule such as a monoclonal antibody having binding affinity for endothelial cell surface antigens, for example. Further, the liposomes may be PEGylated liposomes.

The interfering RNAs may be delivered in solution, in suspension, or in bioerodible or non-bioerodible delivery devices. The interfering RNAs can be delivered alone or as components of defined, covalent conjugates. The interfering RNAs can also be complexed with cationic lipids, cationic peptides, or cationic polymers; complexed with proteins, fusion proteins, or protein domains with nucleic acid binding properties (e.g., protamine); or encapsulated in nanoparticles. Tissue- or cell-specific delivery can be accomplished by the inclusion of an appropriate targeting moiety such as an antibody or antibody fragment.

For ophthalmic, otic, or pulmonary delivery, an interfering RNA may be combined with ophthalmologically, optically, or pulmonary acceptable preservatives, co-solvents, surfactants, viscosity enhancers, penetration enhancers, buffers, sodium chloride, or water to form an aqueous, sterile suspension or solution. Solution formulations may be prepared by dissolving the interfering RNA in a physiologically acceptable isotonic aqueous buffer. Further, the solutions may include an acceptable surfactant to assist in dissolving the inhibitor. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ointment formulation, the interfering RNA is combined with a preservative in an appropriate vehicle, such as mineral oil, liquid lanolin, or white petrolatum. Sterile gel formulations may be prepared by suspending the interfering RNA in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaurate, Sigma Aldrich, St. Louis, Mo.), in the event the interfering RNA is less penetrating in the organ or tissue of interest.

Kits:

Embodiments of the present invention provide a kit that includes reagents for attenuating the expression of an mRNA as cited herein in a cell. The kit contains an siRNA or an shRNA expression vector. For siRNAs and non-viral shRNA expression vectors the kit also may contain a transfection reagent or other suitable delivery vehicle. For viral shRNA expression vectors, the kit may contain the viral vector and/or the necessary components for viral vector production (e.g., a packaging cell line as well as a vector comprising the viral vector template and additional helper vectors for packaging). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and an acceptable carrier. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The ability of TACE- or TNFR1-interfering RNA to knockdown the levels of endogenous TACE or TNFR1 expression in, for example, human corneal epithelial cells is evaluated in vitro as follows. Transformed human corneal epithelial cells, for example, the CEPI-17 cell line (Offord et al. (1999) *Invest Ophthalmol Vis Sci.* 40:1091-1101), are plated 24 h prior to transfection in KGM keratinocyte medium (Cambrex, East Rutherford, N.J.). Transfection is performed using DharmaFECT™ 1 (Dharmacon, Lafayette, Colo.) according to the manufacturer's instructions at TACE- or TNFR1-interfering RNA concentrations ranging from 0.1 nM-100 nM. Non-targeting control interfering RNA and lamin A/C interfering RNA (Dharmacon) are used as controls. Target mRNA levels are assessed by qPCR 24 h post-transfection using, for example, TAQMAN® forward and reverse primers and a probe set that encompasses the target site (Applied Biosystems, Foster City, Calif.). Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of TACE- or TNFR1 interfering RNA is used that produces the desired level of knockdown in target gene expression.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

While a particular embodiment of the invention has been shown and described, numerous variations and alternate embodiments will occur to those skilled in the art. Accordingly, it is intended that the invention be limited only in terms of the appended claims.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

Example 1

Interfering RNA for Specifically Silencing TNFR1 in GTM-3 Cells

The present study examines the ability of TNFR1 interfering RNA to knock down the levels of endogenous TNFR1 protein expression in cultured GTM-3 cells.

Transfection of GTM-3 cells (Pang, I. H. et al., 1994. *Curr. Eye Res.* 13:51-63) was accomplished using standard in vitro concentrations (0.1-10 nM) of TNFR1 siRNAs, siCONTROL RISC-free siRNA #1, or siCONTROL Non-targeting siRNA #2 (NTC2) and DHARMAFECT® #1 transfection reagent (Dharmacon, Lafayette, Colo.). All siRNAs were dissolved in 1× siRNA buffer, an aqueous solution of 20 mM KCl, 6 mM HEPES (pH 7.5), 0.2 mM $MgCl_2$. Control samples included a buffer control in which the volume of siRNA was replaced with an equal volume of 1× siRNA buffer (-siRNA). Western blots using an anti-TNFR1 antibody (Santa Cruz Biotechnology, Santa Cruz, Calif.) were performed to assess TNFR1 protein expression. The TNFR1 siRNAs are double-stranded interfering RNAs having specificity for the following targets: siTNFR1 #1 targets the sequence CAAAGGAACCUACUUGUAC (SEQ ID NO: 202); siTNFR1 #2 targets the sequence GAGCUUGAAGGAACUACUA (SEQ ID NO: 203); siTNFR1 #3 targets the sequence CACAGAGCCUAGACACUGA (SEQ ID NO: 204); siTNFR1 #4 targets the sequence UCCAAGCUCUACUCCAUUG (SEQ ID NO: 205). As shown by the data in FIG. 1, siTNFR1 #1, siTNFR1 #2, and siTNFR1 #3 siRNAs reduced TNFR1 protein expression significantly at the 10 nM and 1 nM concentrations relative to the control siRNAs, but exhibited reduced efficacy at 0.1 nM. The siTNFR1 #2 and siTNFR1 #3 siRNAs were particularly effective. The siTNFR1 #4 siRNA also showed a concentration dependent reduction in TNFR1 protein expression as expected.

What is claimed is:

1. A method of treating a TNFα-related ocular condition in a subject in need thereof, comprising:
administering to an eye of the subject a composition beginning at an effective amount of interfering RNA having a length of 19 to 49 nucleotides, and a pharmaceutically acceptable carrier, the interfering RNA comprising a sense nucleotide strand, an antisense nucleotide strand, and the sense and antisense strands comprise a region of least near-perfect contiguous complementarity of at least 19 nucleotides;
wherein the antisense strand hybridizes under physiological conditions to a portion of mRNA corresponding to SEQ ID NO:2 comprising nucleotide 2048;
wherein the TNFα-related ocular condition is treated thereby, and wherein the TNFα-related ocular condition is dry eye, allergic conjunctivitis or ocular inflammation.

2. The method of claim 1, wherein the sense nucleotide strand and the antisense nucleotide strand are connected by a loop nucleotide strand.

3. The method of claim 1, wherein the composition is administered via an intraocular ocular, or tropical route.

4. The method of claim 1, wherein the interfering RNA is administered via in vivo expression from an expression vector capable of expressing the interfering RNA.

5. The method of claim 1, wherein each strand of the siRNA molecule is independently about 19 nucleotides to about 25 nucleotides in length.

6. The method of claim 1, wherein each strand of the siRNA molecule is independently about 19 nucleotides to about 21 nucleotides in length.

* * * * *